(12) United States Patent
Yamashita et al.

(10) Patent No.: US 7,187,961 B2
(45) Date of Patent: Mar. 6, 2007

(54) SEMICONDUCTOR DEVICE FOR SENSOR SYSTEM

(75) Inventors: Shunzo Yamashita, Musashino (JP); Kei Suzuki, Kokubunji (JP); Toshiyuki Aritsuka, Kodaira (JP); Masayuki Miyazaki, Tokyo (JP); Sadaki Nakano, Kokubunji (JP)

(73) Assignee: Hitachi, Ltd., Tokyo (JP)

( * ) Notice: Subject to any disclaimer, the term of this patent is extended or adjusted under 35 U.S.C. 154(b) by 463 days.

(21) Appl. No.: 10/457,498

(22) Filed: Jun. 10, 2003

(65) Prior Publication Data

US 2004/0000713 A1 Jan. 1, 2004

(30) Foreign Application Priority Data

Jun. 26, 2002 (JP) ............................ P2002-185450

(51) Int. Cl.
*A61B 5/00* (2006.01)
(52) U.S. Cl. ...................... 600/310; 600/300; 600/549; 600/595; 128/903
(58) Field of Classification Search ................ 600/300, 600/310, 549, 595; 128/903
See application file for complete search history.

(56) References Cited

U.S. PATENT DOCUMENTS

| | | | | |
|---|---|---|---|---|
| 5,862,803 A | * | 1/1999 | Besson et al. ............... | 600/508 |
| 6,402,689 B1 | * | 6/2002 | Scarantino et al. .......... | 600/300 |
| 6,441,747 B1 | * | 8/2002 | Khair et al. ................. | 128/903 |
| 2001/0049471 A1 | | 12/2001 | Suzuki et al. | |
| 2002/0028988 A1 | | 3/2002 | Suzuki et al. | |

FOREIGN PATENT DOCUMENTS

| | | |
|---|---|---|
| JP | 05-293128 | 11/1993 |
| JP | 2001-187611 | 7/2001 |
| JP | 2001-327472 | 11/2001 |
| JP | 2001-344353 | 12/2001 |
| JP | 2002-058648 | 2/2002 |

OTHER PUBLICATIONS

"A Child of Revolution of Wireless Who Is Born, "Ultra Wideband"", Nikkei Electronics Mar. 11, 2002, p. 55.
"Opening a Frontier of Wireless World Part 1", Nikkei Electronics Feb. 25, 2002, p. 112.
Graham Prophet, "RF MEMS Technology Makes a Leap by Third-generation Portable Telephone" EDN Japan May 2002, Design Feature.
Jan M. Rabaey et al, "PicoRadio Supports Ad Hoc Ultra-Low Power Wireless Networking", 2000 IEEE.

(Continued)

*Primary Examiner*—Eric F. Winakur
(74) *Attorney, Agent, or Firm*—Antonelli, Terry, Stout and Kraus, LLP.

(57) ABSTRACT

A semiconductor device is employable for a compact and light-weight sensor system that is free of the need for battery replacement. The semiconductor device has a sensor chip (SCHIP1) comprising sensors (TD1, AS1, PD1, GS1), an A/D conversion circuit (AD1), a microprocessor (CPU1), a memory (MEM1), a transmission circuit (RF1), and a power generation circuit (CM1). The sensors, the A/D conversion circuit, the microprocessor, the memory, and the transmission circuit are formed on one side (SIDE1) of a substrate, while the power generation unit is formed on the other side (SIDE2) of the substrate.

17 Claims, 23 Drawing Sheets

OTHER PUBLICATIONS

Scott Meninger, et al "Vibration-to-Electric Energy Conversion", IEEE Transactions on very large Scale Integration (VSLI) Systems, vol. 9, No. 1 Feb. 2001.

EDN Japan FAO May 2002, p. 54.

C. B. Williams, et al., "Development of an Electromagnetic Microgenerator", IEE Proc-Circuits Devices Syst., vol. 148, No. 6, Dec. 2001.

Sokwoo Rhee et al., "The Ring Sensor: a New Ambulatory Wearable Sensor for Twenty-Four Hour Patient Monitoring", Proceedings of the 20th Annual International Conference of the IEEE Engineering in Medicine and Biology Society Hong Kong, Oct. 29-Nov. 1, 1998.

Cover Story, Nikkei Electronics Feb. 25, 2002.

Leading Trends, "Ultra Wideband", Nikkei Electronics Mar. 11, 2002.

* cited by examiner

| CID | SID | DATA |
|---|---|---|
| #1 | #1 | $1.0 \times 10^{-9}$ |
| #1 | #3 | $2.1 \times 10^{1}$ |
| #2 | #2 | $3.5 \times 10^{1}$ |
| #3 | #1 | $3.5 \times 10^{1}$ |
| ⋮ | ⋮ | ⋮ |

SD1

SEMICONDUCTOR DEVICE FOR SENSOR SYSTEM

BACKGROUND OF THE INVENTION

The present invention relates to a semiconductor device for use in sensor systems. More particularly, the present invention relates to a semiconductor device to be employed for compact and light sensor systems that are free of the need for battery replacement.

In recent years, people have come to be more mindful of requisites to good health; and, accordingly, they are seeing the need for various personal vital assistant instruments (hereinafter, to be described as "PVA" instruments) that facilitate the users in making it easier to perform health checks by themselves. The functions of these PVA instruments are similar to those of conventional expensive medical measuring instruments. However, unlike those expensive medical instruments, such PVA instruments need to be supplied at lower prices, so that the general public is able to purchase them. In addition, for patients of lifestyle-related illnesses, it is important for them to monitor their bodily temperatures and blood pressures continuously. To meet such requirements, PVA instruments also need to be simplified in configuration so that the users can measure their health conditions easily. More particularly, PVA instruments should be compact and light so that the users can carry them with them. To meet such requirements, PVA instruments that are housed in compact boards are now under development.

For example, such PVA instruments are disclosed in the official gazettes of JP-A No. 327472/2001 (hereinafter to be referred to as [document 1]) and JP-A No. 344352/2001 (hereinafter to be referred to as [document 2]). Each of the PVA instruments comprises a GSR (Galvanic Skin Reflex) electrode; a sensor board in which an acceleration sensor, a bodily temperature sensor, a blood pulse sensor, etc. are built; and a main board for communicating with the sensor board to collect sensor information through a Bluetooth low power wireless interface, for example, to analyze the physical condition, etc. of the user. In addition to the above-described sensors, the sensor board also includes a CPU, a memory, an A/D converter, a low power wireless interface, an amplifier, and a small battery. Furthermore, a dedicated board is provided for each of the sensors located on the sensor board. Information (analog values) received from each sensor located on the sensor board is amplified to a proper level, then converted to digital values in the A/D converter, and finally processed to information in a proper format by the CPU and transmitted to the main module through the low power wireless interface chip.

Among the above-mentioned sensors, the blood pulse sensor can detect changes in the state of the electrical impedance of the user's skin, as detected through a GSR electrode, whereby the user's mental condition or state (anger, etc.) can be determined. The blood pulse sensor can also measure the degree of saturation of the oxygen in the user's blood. In addition, the blood pulse sensor can also estimate the blood sugar level of the user and indicate the user's physical condition. Blood pulse intervals of the user make it possible to estimate the user's mental state to a certain degree. The blood pulse sensor is configured by a pair of elements, including an infrared/red LED and a semiconductor photo-diode. On the other hand, the acceleration sensor is configured by acceleration sensors of three axial directions, and it is used to estimate the posture, motion, or the like of the user. The user can thus know the diagnostic result transmitted to his/her wrist watch, headset, portable telephone, or similar device through its built-in low power wireless interface.

On the other hand, an RFID chip, which is configured by a simple RF circuit, a low performance CPU, and a low capacity memory (non-volatile memory or the like), that are integrated in a semiconductor integrated circuit having a size which is a few millimeters square and under, is disclosed in Nikkei Electronics (Feb. 25, 2002, pp. 112–137 (hereinafter to be referred to as [document 3]). The RFID chip disclosed in the document 3 has its specific ID written in its built-in non-volatile memory and the ID is read through an RF reader, so that the RFID chip is used as an identification tag for a product, just like a barcode. More specifically, such an ID is read through a RFID reader by detecting the Q value of an LC oscillation circuit that is configured by a coil and a capacitor to be changed by a high frequency irradiated on the RFID chip. This detection is carried out in a non-contact manner.

In addition to such an ID, product information or the like also can be written in the non-volatile memory of the RFID chip. For example, as disclosed in the official gazette of JP-A No. 187611/2001 (hereinafter to be described as [document 4]), such an RFID chip is applied to a food (ex., beer barrels, etc.) distribution management system. In the system disclosed in document 4, an RFID chip, a sensor board, and an ID tag provided with a sensor configured by a small battery are embedded in each beer barrel and the temperature of the beer barrel read by the sensor is written and stored as needed in the non-volatile memory located in the RFID chip. And, when the beer barrel is delivered to the user, the user reads the temperature information, stored during the delivery, through use of an RF reader. Such a configuration of the RFID chip makes it possible for the user to know whether or not the temperature of the beer barrel has been controlled properly during the transportation through the electronically recorded information read from the chip.

On the other hand, the official gazette of JP-A No. 58648/2002 (hereinafter to be referred to as [document 5]) discloses an example of the use of an RFID chip for locating positions. In this example, an RFID chip is attached to each of a plurality of animals, such as mice used for experiments. In this connection, a mouse cage is divided into small square areas and a plurality of RFID readers are arranged so that one RFID reader is disposed in each of the square areas. Then, information read by each of the plurality of RFID readers is registered continuously to detect the movement of a target mouse. The ID information of each RFID chip can also be used more effectively to distinguish among mice individually. In this case, the configuration of the RFID chip makes it possible to determine how each mouse is moving in the cage individually.

There have also been some attempts in which such semiconductor microchips are embedded in a user's body, so that the user can obtain auxiliary helpful information from the microchips. For example, the official gazette of JP-A No. 293128/5 (hereinafter to be referred to as [document 6]) discloses a technique in which microchips are embedded in the vocal organ of a user, so that vibration of the vocal cords is detected and transmitted through an RF circuit to an external pseudo voice generation apparatus, so as to artificially produce vocal sounds, instead of by means of the user's vocal cords. More specifically, the chips are embedded in a plurality of positions, such as the pharynx, the larynx, the respiratory tract, the face, the mouth, the nasal cavity, etc. so that the vibration sensor in each chip detects the vibration at each of these positions, thereby to enable the pseudo voice generation apparatus to analyze the vocal sounds the user wants to utter. This will become a great help for the user whose vocal cords have been damaged.

The IEEE Computer July 2000 (pp. 42–48 (hereinafter to be described as [document 7]) also recognizes an effect in which floors, walls, human bodies, etc. are always vibrating slightly, so that each of those items usually has an energy density of about mW/cm3.

On the other hand, a configuration of a power collection circuit is disclosed in the IEEE TRANSACTIONS ON VERY LARGE SCALE INTEGRATION SYSTEMS, VOL. 9, NO. 1, February 2001 (pp. 64–75) (hereinafter to be referred to as [document 8])).

A high frequency switch formed in the MEMS process is disclosed in EDN Japan, 2002, No. 5 (pp. 55–61) (hereinafter to be referred to as [document 9]).

A UWB (Ultra Wide Band) radio communication method is disclosed in Nikkei Electronics, Mar. 11, 2002 (pp. 55–66) (hereinafter to be referred to as [document 10]). According to the technique described in this document 10, a correlator is needed for receiving data in the UWB. The correlator correlates pulse strings supplied from a receiver pulse generator with received pulse strings.

A power generator that generates electric power through electromagnetic inductance is disclosed in IEEE Proc. Circuits Devices Syst., Vol. 148, No. 6 December 2001 (hereinafter to be referred to as [document 11]).

The PVA instrument disclosed in each of the documents 1 and 2 uses a general CPU and a sensor board. The PVA instrument thus makes it easier for the user to perform his/her health management without using any expensive medical instrument. Such a PVA instrument, however, needs a battery for both the sensor board and the main board, respectively. The instrument thus comes to become very heavy (up to a few hundreds of grams). Because a plurality of semiconductor circuits and other circuits are assembled on a board, it is unavoidable that the instrument will increase in size to a certain extent (up to the card size). Consequently, the burden on the user increases, particularly when the user uses the PVA instrument for a long time. In addition, because the PVA instrument is powered by a battery, the user is required to periodically replace the battery. And, while each sensor is connected to the main board wirelessly through a low power wireless interface, each sensor is also connected to the sensor board through an ordinary wire, so that the PVA instrument comes to face some minor difficulties and problems in both operation and durability.

On the other hand, the RFID chip disclosed in the document 3 does not need any battery, and it is compact in size. Thus, it can be attached to various objects, such as small animals, like mice, human beings, food products, etc. However, as described in connection with the conventional techniques, because the Q value of the LC resonant circuit is controlled to transmit signals to each RFID reader, the size of the external inductor L is determined by the subject RF signal wavelength (=1/frequency). And, because it does not have its own power source, it is operated only when RF signals are applied to the RFID chip from each RFID reader. This is why the RFID chip is considered to be not suitable for detecting information from the user's living body (bodily temperature, blood pulse, etc.) over a long period of time, since such a long time detection is indispensable for the PVA instruments.

The RFID tag to be attached on each beer barrel disclosed in the document 4 is provided with a small battery so as to keep it working for a long time. As a result, the RFID chip size is limited only in the card size, so that the feature of the RFID chip that "a compact and light-weight tag can be stuck at any place" is sacrificed.

In the document 5, such an RFID chip is used to detect the movement of each mouse. In this connection, the RFID reader disposed in each of the square areas is required to keep transmitting RF signals. The power of the RF signal transmitted from each RFID reader is about a few hundreds of milliwatts, so that the total power becomes a considerably large value. This makes it difficult to realize low power consumption in the RFID chip.

In the document 6, semiconductor microchips are embedded in a human body so as to realize a pseudo voice generating device. To embed semiconductor microchips in the human body in such a way, surgery is needed. The user's physical and mental burdens will thus increase significantly. However, the document 6 discloses no concrete configuration for the embedded semiconductor chips, nor does it disclose how to power the chips when no battery is embedded together with those chips, although this is a very important item.

SUMMARY OF THE INVENTION

Under such circumstances, it is an object of the present invention to provide a semiconductor device that is employable for compact and light-weight sensor systems, each of which can transmit detected data to external devices with the use of radio signals. The sensor system is assumed to have a built-in power generator and to enable long time operation.

It is another object of the present invention to provide a control unit that uses the above-described semiconductor device for controlling such instruments as compact health care instruments, motion detectors, food distribution management apparatuses, home electrical appliances, etc.

According to one aspect of the present invention, the semiconductor device of the present invention comprises a sensor for detecting a physical quantity from an object of measurement, an A/D conversion circuit for amplifying a signal detected by the sensor and for converting it to a digital signal, a microprocessor for processing the digital signal, a memory for storing the information obtained from the sensor, a transmission circuit for transmitting signals processed by the microprocessor, and a power generator for generating electrical power to be supplied to each of the sensor, the A/D conversion circuit, the microprocessor, the memory, and the transmission circuit.

According to another aspect of the present invention, the semiconductor device of the present invention comprises a sensor chip, that includes a temperature sensor, an acceleration sensor, and a red/infrared ray sensor; an A/D conversion circuit for amplifying signals received from the sensors and for converting them to digital signals; a microprocessor for taking out information from the sensors so as to process the information; a memory for storing a program code of the microprocessor and information received from the sensors; a transmission circuit that is controlled by the microprocessor and used to communicate with external devices; a power supply control circuit for controlling whether to supply electric power to each of the sensor chip, the A/D conversion circuit, the microprocessor, the memory, and the transmission circuit; and a power collection circuit for collecting an increase in the electrostatic energy of a variable capacitor, which is generated by mechanical vibration. The sensor chip, the A/D conversion circuit, the microprocessor, the memory, and the transmission circuit, and the power supply control circuit are formed on one semiconductor substrate.

According to still another aspect of the present invention, the semiconductor device of the present invention includes a microprocessor, a memory for storing information, and a transmission/reception circuit for transmitting/receiving data to/from the microprocessor, are all of which are formed on one semiconductor substrate. The semiconductor device further includes a power generator for generating electric power to be supplied to each of the microprocessor, the memory, and the transmission circuit. Furthermore, the semiconductor has functions to receive first data from a first external device and to convert the received first data to second data to be transmitted to a second external device, that is different from the first external device.

DETAILED DESCRIPTION OF THE PREFERRED EMBODIMENTS

Figure 1A:
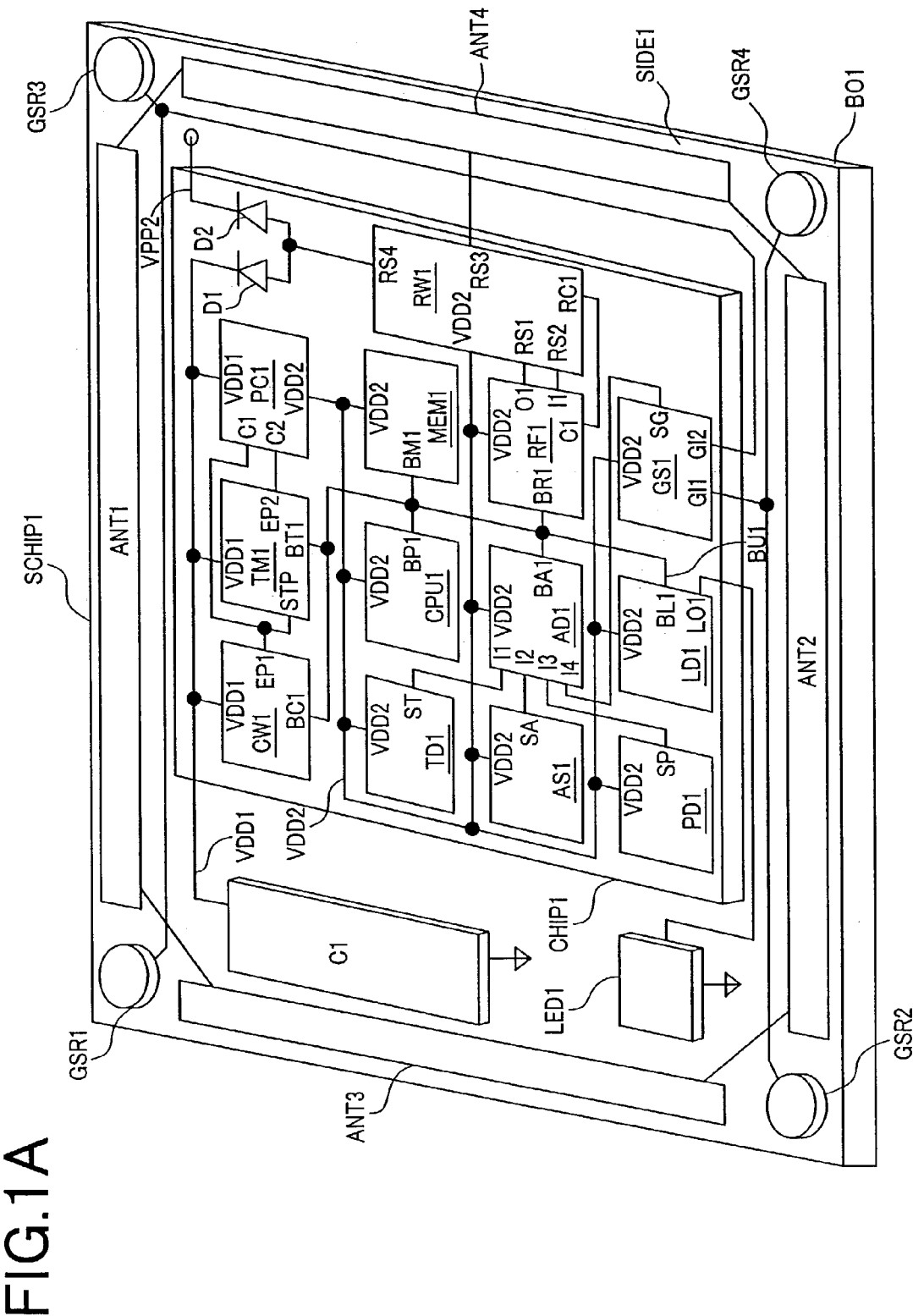
FIG. 1A is a diagrammatic perspective view of the top side of a sensor chip representing a preferred embodiment of the present invention.

Hereunder, the preferred embodiments of the present invention will be described in detail with reference to the accompanying drawings. In the drawings, the same numerals/symbols will be used to identify the same functional components/parts.

First Embodiment

Figure 1B:
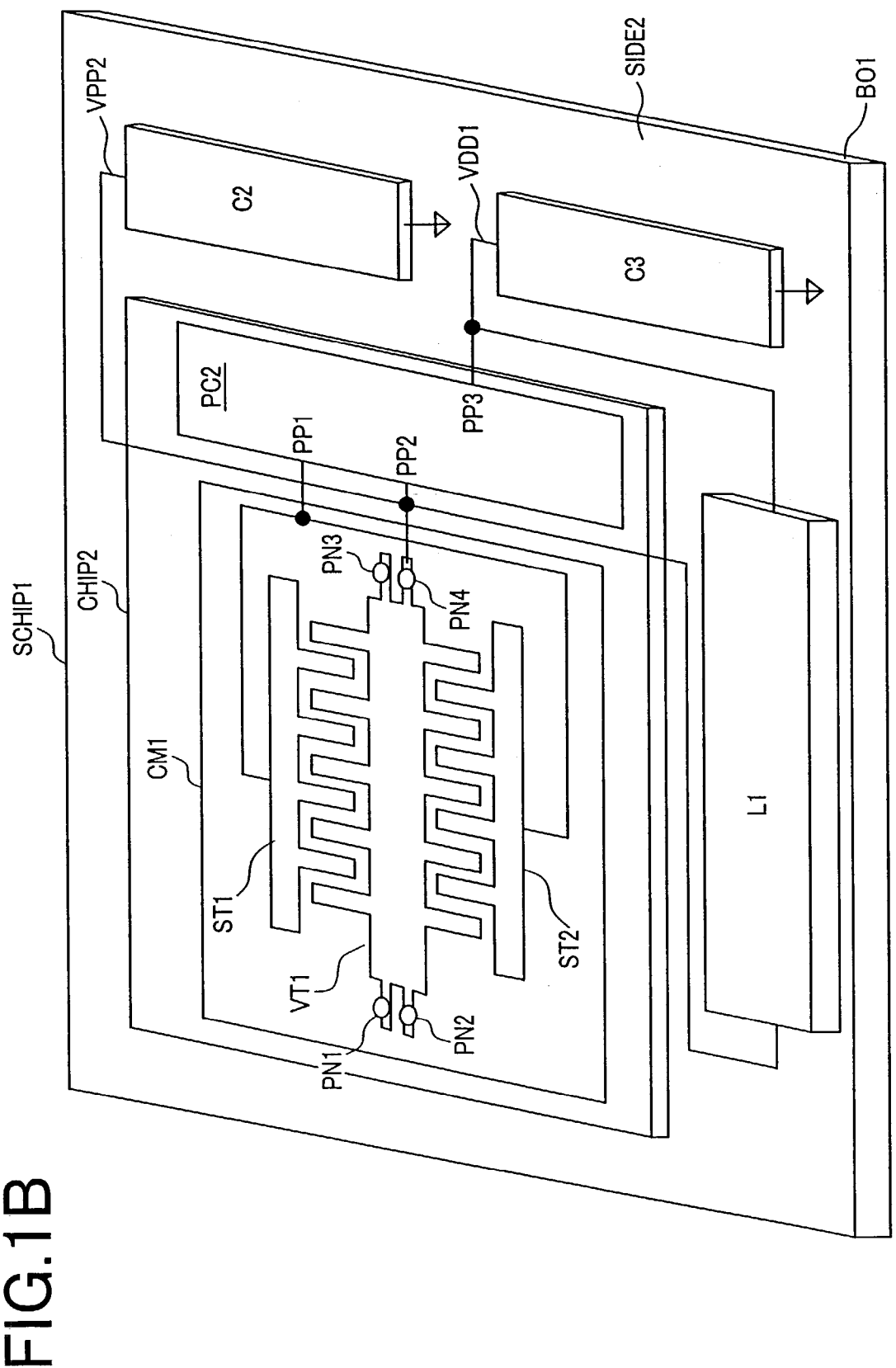
FIG. 1B is a diagrammatic perspective view of the bottom side of the sensor chip in the preferred embodiment of the present invention.

FIGS. 1A and 1B are block diagrams of a semiconductor device for a sensor system, that is, a sensor chip. FIG. 1A shows one main side (SIDE1) of the sensor chip, while FIG. 1B shows the other main side (SIDE2), that is the back side thereof. The sensor chip (SCHIP1) comprises a first semiconductor integrated circuit (CHIP1), a second semiconductor integrated circuit (CHIP2), a light emission diode (LED) chip (LED1), capacitors (C1 to C3), an inductor (L1), and a substrate (BO1) for mounting those chips and parts. The substrate (BO1) has wiring patterns for the connection among those chips, antenna patterns (ANT1 to 4) for use by a high frequency transmission/reception circuit (to be described later), and electrode patterns (GSR1 to 4) for use by a sensor circuit (GS1) (to be described later). Those patterns are formed with such metal materials as copper, gold, or the like. The chips and patterns are similar to those used usually for MCP (Multi Chip Package) chips.

Figure 2A:
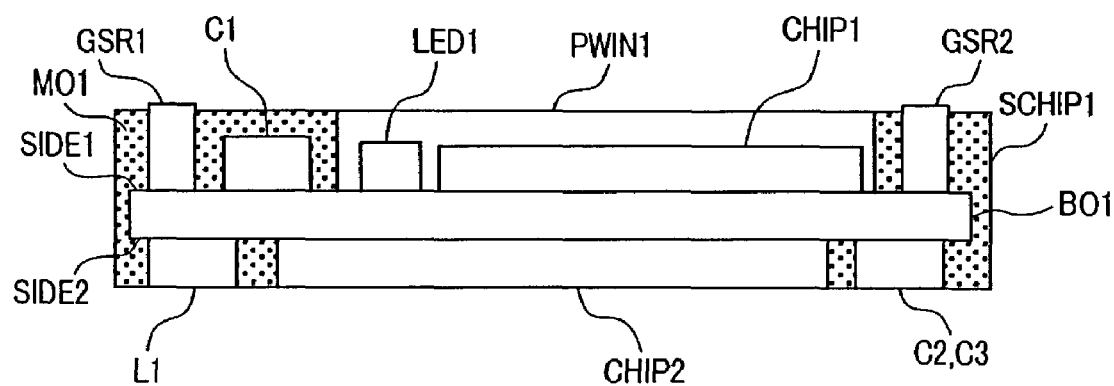
FIG. 2A is a cross sectional view of the sensor chip shown in FIGS. 1A and 1B.
Figure 2B:
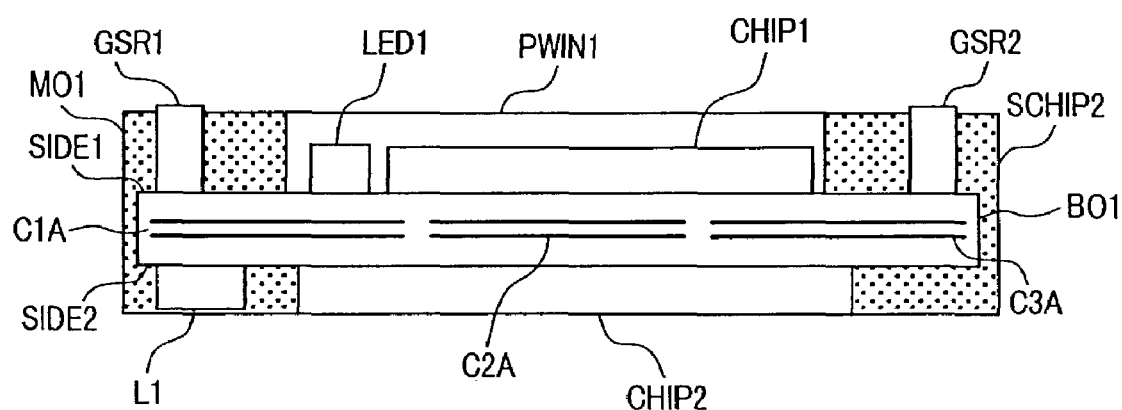
FIG. 2B is a cross sectional view of the sensor chip shown in FIGS. 1A and 1B.

FIGS. 2A and 2B show cross sectional views of the sensor chip. As shown in FIGS. 2A and 2B, the first and second semiconductor integrated circuits (CHIP1) and (CHIP2) are mounted on the substrate (BO1), characteristic to the present invention. In other words, CHIP1 and CHIP 2 are mounted separately on different surfaces (SIDE1) and (SIDE2) of the substrate. And, as shown in FIGS. 2A and 2B, the CHIP1 and CHIP2, as well as the capacitors, the inductor, and the substrate are molded by water-proof resin (MO1), and, thus, they are water-resistant. Those molds may be any of the type used in conventional MCP chips. However, unlike the molds of the conventional MCP chips, the CHIP1 has an optical window that is a characteristic of the present invention; and, the optical window is formed on the top surface of the CHIP1 with a molding material that transmits red/infrared rays. More specifically, this optical window (PWIN1) is formed on the dedicated photo-sensors located on the LED1 and the CHIP1, as mounted on the substrate MO1 respectively. This is to enable the dedicated photo-sensor provided on the CHIP1 to detect reflected light of the red or infrared rays that are emitted from the LED1 to the outside.

And, the capacitors (C1 to C3) and the inductor (L1) shown in FIG. 2A may belong to the same chip type used for conventional MCP chips. The capacitors (C1 to C3) may also be laminated ones (C1A to C3A) configured by using some of the layers of the substrate formed as a multilayer structure. In this connection, layers of each laminated capacitor are paired. Thus, a compact and light portable health care instrument can be realized using a sensor chip (SCHIP1) formed with those semiconductor integrated circuits (CHIP1 and CHIP2).

Figure 3:
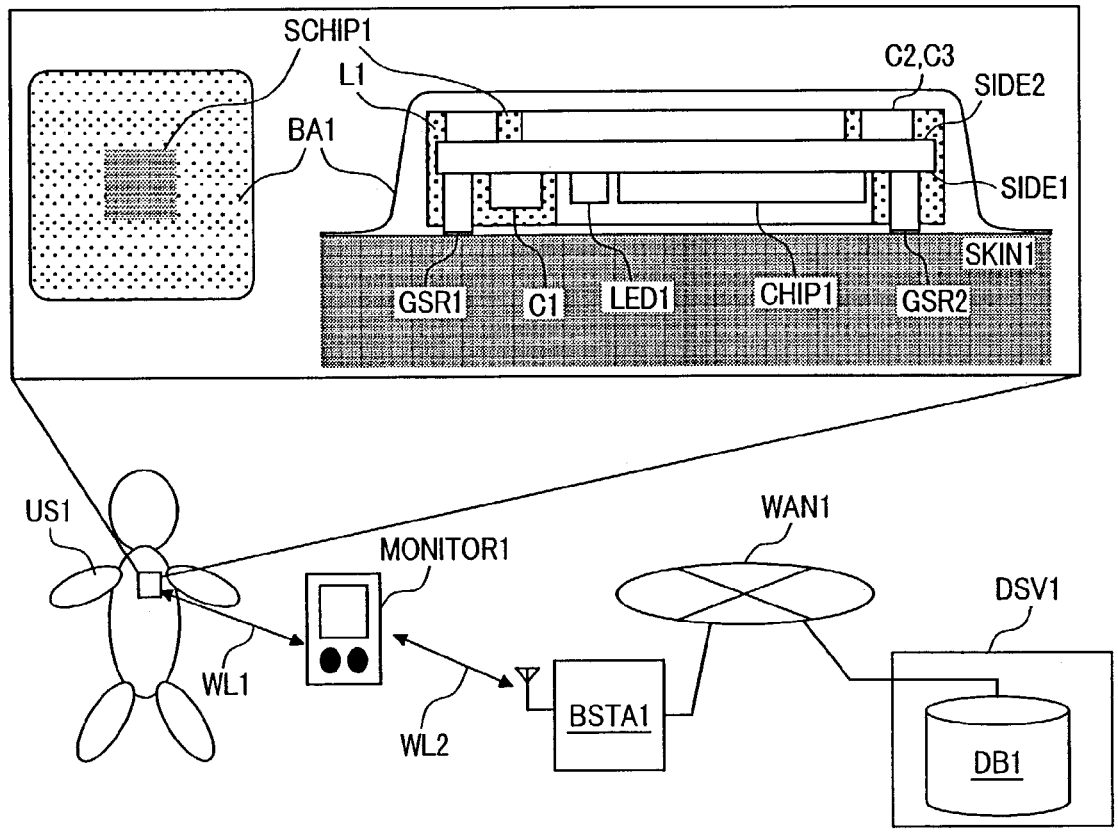
FIG. 3 is a diagram of a health care instrument that uses the sensor chip of the present invention according to a first embodiment of the present invention.

FIG. 3 shows an example of a sensor chip employed for a health care instrument. In this example, the sensor chip can be stuck on the skin (SKIN1) of the user (US1) with the use of a seal (BA1), such as an adhesive plaster. The SIDE1 of the sensor chip comes in contact with the user's skin. Consequently, the user's physical and other health conditions can be detected by various sensors (to be described later). In this example, while a seal BA1, such as an adhesive plaster, is used to stick the sensor chip on the user's skin, the present invention is not limited only to such an example; the seal BA1 may be replaced with any means that can make the sensor chip come in contact with the user's skin, for example. For example, the sensor chip may be stuck on the back side of a wrist watch.

Detected data is transmitted to an external health monitor (MONITOR1) or the like wirelessly (WL1) through the microprocessor CPU1 and the high frequency transmission/reception circuit RF1 located in the first semiconductor integrated circuit CHIP1. As seen in FIG. 1A, the first semiconductor integrated circuit(CHIP1) is configured by a microprocessor (CPU1), a memory (MEM1), a high frequency transmission/reception circuit (RF1) for transmitting/receiving data to/from the outside, a high frequency switch (RW1) for switching between transmission and reception of each of the antennas (ANT1 to 4) provided on the substrate (BO1), a sensor circuit composed of a temperature sensor (TD1), an acceleration sensor (AS1), a red/infrared ray sensor (PD1), an impedance sensor (GS1), etc., an A/D conversion circuit (AD1) for converting signals received from the sensors to digital signals, a driver (LD1) for driving the light emission diode (LED1) mounted on the substrate, a power supply control circuit (PC1) for controlling whether to supply an electric power to each of the CPU1, the MEM1, the RF1, the RW1, TD1, the AS1, the PD1, and the GS1, a timer circuit (TM1) for controlling the on/off state of the PC1, and an electric charge monitoring circuit (CW1) for monitoring the electric charge accumulated in the capacitor C1.

The microprocessor CPU1 controls the operation mode of each circuit on the chip under the control of a program (PR1) stored in the memory MEM1 to drive each sensor for detection. And, as will be described later, detected data is compressed or processed so as to add ID information to the data, and then it is transmitted to the outside wirelessly through the high frequency transmission/reception circuit RF1. In addition, the set operation mode parameters can be updated in the microprocessor CPU1. A proper program code can be added to the program PR1 so as to add a given processing to the program PR1.

The memory MEM1 retains the program PR1, as well as data obtained from each sensor, and such information as operation mode parameters to be set in the microprocessor CPU1. The memory MEM1 is configured typically by an SRAM that can retain data at low power consumption, as well as a NOR or AND type flash memory that can keep data even at the time of power off. The MEM1 may be replaced with any type memory, however, so long as it can retain data at low power consumption.

The second semiconductor integrated circuit (CHIP2) is a power generation microchip for generating electric power by converting weak external vibrations to electrical energy. As disclosed in the document 7, the CHIP2 generates a power of about 0.1 mW using the external vibration energy transmitted from a floor, a wall, a human body, etc. Hereinafter, the operation of the power generation chip of the present invention will be described in detail.

As seen in FIG. 2B, the power generation chip CHIP2 is configured by a variable capacitor (CM1), the capacitance of which varies in response to external vibrations, as well as a power collection circuit (PC2). The power collection circuit PC2 collects electrical energy that has been converted from the mechanical energy of the external vibration by the variable capacitor CM1 to charge the capacitor (C3) that is provided on the substrate. The variable capacitor CM1 is usually formed minutely on a silicon chip in the MEMS process. More specifically, as shown in FIG. 1B, the CM1 is configured by two fixed electrodes (ST1, ST2) and a movable electrode (VT1). The movable electrode (VT1) is not fixed anywhere except at anchors (PN1 to 4), so that the movable electrode VT1 floats above the CHIP2. As a result, an inertial force is generated and the force causes vibration to occur between the two fixed electrodes (ST1 and ST2). This vibration causes the distance between the two fixed electrodes to change, whereby the capacitance changes.

Figure 4:
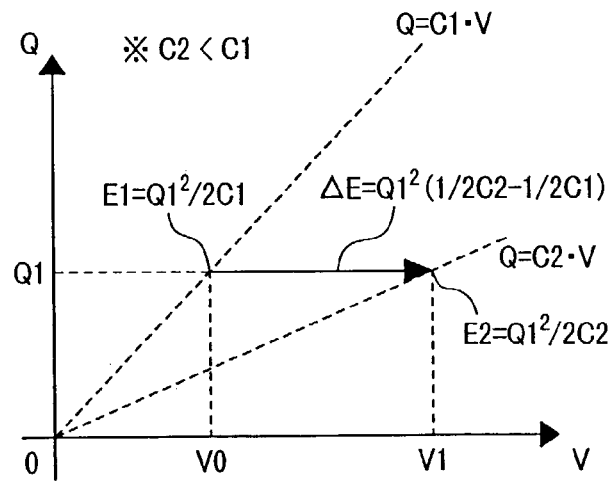
FIG. 4 is a graph of voltage changes and an increase of electrostatic energy when the capacitance of a variable capacitor used in the sensor chip of the present invention is changed by external vibration.

FIG. 4 is a graph showing changes of the voltage V(V0->V1) and the electrostatic energy (E1->E2) according to a change (C1->C2(C2<C1)) of the CM1 capacitance caused by external vibration, when the charge Q of the variable capacitor (CM1) is fixed at Q1. If the capacitance is changed by external vibration in this way, the accumulated electrostatic energy increases (ΔE=E2−E1). And, the increase Δ of this electrostatic energy is collected to cause the power generation chip CHIP2 to function as a compact power generation circuit.

Figure 5:
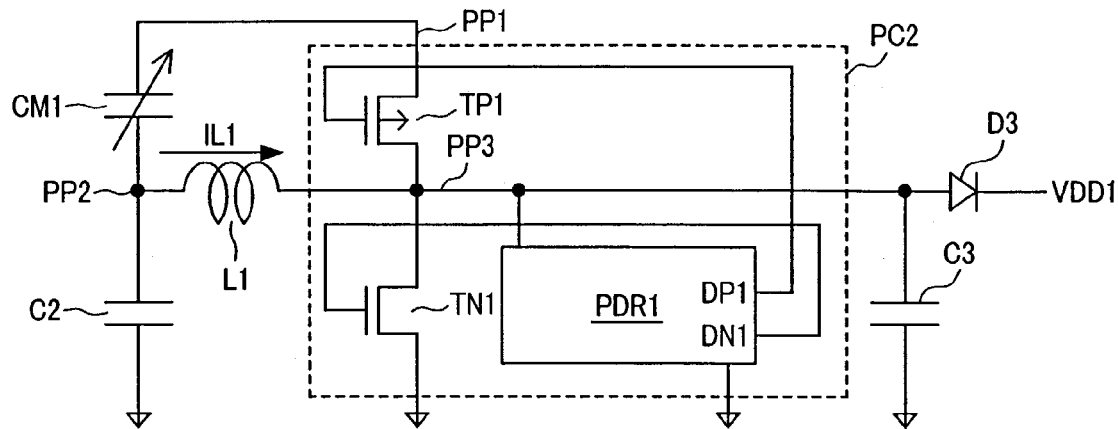
FIG. 5 is a schematic diagram of a power collection circuit that collects an increase of the electrostatic energy shown in FIG. 4, which is to be converted to electric power.
Figure 6:
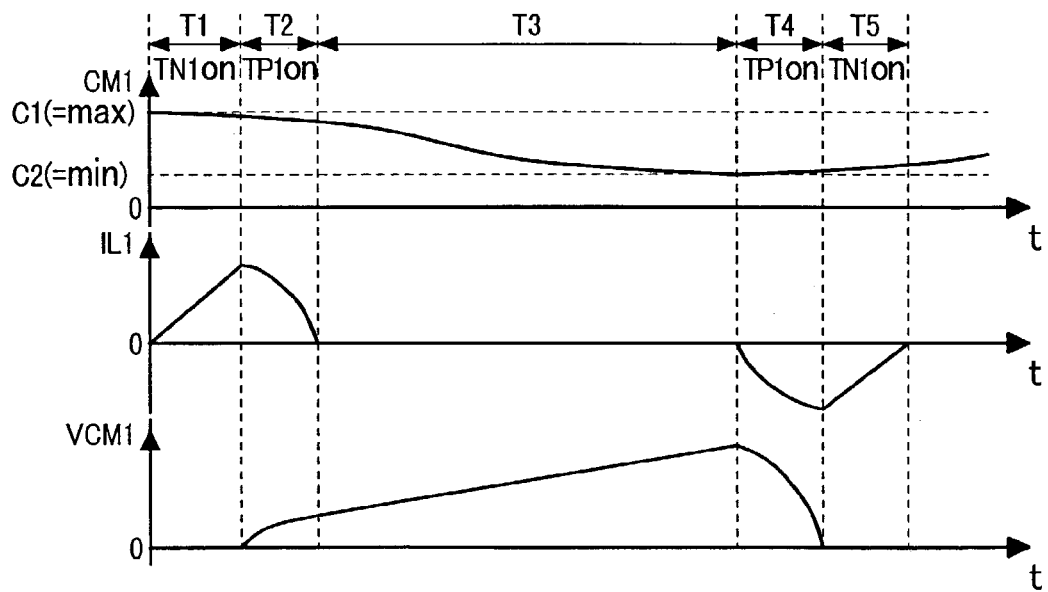
FIG. 6 is a graph of the operation of the power collection circuit shown in FIG. 5.

FIG. 5 shows an example of the power collection circuit formed in the CHIP2. This circuit is configured similarly to that disclosed in the document 8. In addition to the variable capacitor CM1, the power collection circuit includes capacitors C2 and C3, an inductor L1, a PMOS transistor TP1, an NMOS transistor TN1, and a drive circuit (PDR1) for controlling the on/off timings of those transistors. The drive circuit PDR1 controls the timings (T1 to T5) and the on/off timings of the transistor TN1 and the transistor TP1 according to the changes of the capacitance of the variable capacitor CM1 caused by external vibration. The operation of the power collection circuit is not a characteristic of the present invention, and so the description for the circuit will be omitted here.

The generated power is supplied to the VDD1 line through the capacitor C3 and the diode D3 in the final step, whereby the generated power charges the capacitor C1 connected to the power supply control circuit PC1 of the first semiconductor integrated circuit CHIP1. Although the capacitor C2 charges the capacitor CM1 initially, the capacitor C2 itself must be charged initially. In the sensor chip of the present invention, therefore, the capacitor C2 is charged by a high frequency power inducted from the outside by an RFID reader or the like in a non-contact manner through any of the antennas (ANT1 to 4) and the rectifier (D2).

The variable capacitor CM1 can be manufactured in the MEMS process that is compatible with the semiconductor process. Consequently, the capacitor CM1 can also be integrated together with other parts in one semiconductor integrated circuit. As shown in FIG. 4, however, the power energy to be taken out depends on the two values, that is, the capacitance (a difference between the maximum capacitance C2 and the minimum capacitance C1) of the capacitor CM1 and the initial charge Q. In other words, the larger the capacitance of the capacitor CM1 is and the larger the initial charge Q is, the more will be the electric energy that is taken out. Consequently, the larger the capacitance is, the more the capacitance becomes favorable for the present invention. Usually, the capacitance should be about a few hundred picofarads. To increase the capacitance, the area of the CM1 shown in FIG. 1 is expanded, or the groove area formed like a comb by the electrodes disposed therein is more greatly deepened. This is why the CM1 area should be about 1 cm×1 cm×0.5 mm (depth) in size.

The comb-like groove area is formed by etching. In the case of conventional semiconductor integrated circuits, however, the etching is usually not so deep as 5 mm. In spite of this, the deeper the groove area is formed, the more the area becomes favorable for the present invention from the aspect of the power generation efficiency. On the other hand, from the aspect of the manufacturing cost of the semiconductor integrated circuits, the smaller the area of the capacitor CM1 is, the more it becomes favorable. And, the etching for grooving should preferably not be so deep.

To solve this contradiction, the sensor chip of the present invention is configured by two chips (semiconductor integrated circuits), as shown in FIG. 1, so that the variable capacitor CM1 and the power generation circuit are formed on one chip, and other circuits are formed on the other chip. Because of this two-chip configuration, each of the two chips can be manufactured in a dedicated process, thereby the comb-like groove areas of the two chips are formed at different depths. In addition, those two chips are mounted on different sides (SIDE1 and SIDE2) of a substrate that is formed in the MCP configuration characteristic to the present invention. Consequently, the area of the variable capacitor CM1 increases approximately up to that of the sensor chip, whereby the capacitance of the CM1 increases significantly. In addition, as shown in FIG. 1, it is possible to mount the capacitors (C2 and C3) that are indispensable in the power collection circuit, as well as the LED chip and the GSR electrodes that are required in the sensor circuit, and the antennas required in the high frequency transmission/reception circuit, in another area of the substrate BO1, or to form them as wiring patterns. In other words, because of the configuration shown in FIG. 1, which is characteristic of the present invention, it is possible to realize a sensor system in which a power generator, sensors, a CPU, and an RF circuit are integrated in an area roughly equal to the chip size (up to 1 cm square). This is why the present invention can realize an autonomous sensor system as described above.

And, the sensor chip of the present invention is powered autonomously, as described above. According to any conventional technique, however, the power to be generated is limited only to about 1 mW per sensor chip of about 1 cm square in size. On the other hand, for a semiconductor integrated circuit that is manufactured in the CMOS process, if the clock frequency for both microprocessor and memory (especially SRAM) has fallen to about 100 kHz, the power consumption is reduced up to a few tens of micron watts. In this embodiment, the maximum-loaded processing of the microprocessor is only data compression, so that a clock frequency of about 100 kHz will be enough to perform the data compression. (For example, a clock frequency of a few hundreds of kilohertz could execute 100,000 cycles of instructions per second. One hundred cycles of instructions can be executed per millisecond.) Consequently, the above-described power generation chip can supply an electric power sufficient to operate all of the microprocessor, the memory, and other circuits.

Nevertheless, if a high frequency is used to communicate wirelessly with the outside, about 1 mW RF output is required even for such a low power wireless interface as a so-called low power consumption Bluetooth one. Actually, an RF power addition efficiency of 50% can convert a supply electric power to RF, so that a few milliseconds of watts come to be required. And, to satisfy such requirements, various lower power consumption radio communication methods have been proposed conventionally and a power supply of about 1 mW is still needed. And, as described above, the RF part is the largest electric power consumer. This is why the weak electric power supplied from the above power generation chip is far insufficient to carry out high frequency communications with the outside.

Figure 7:
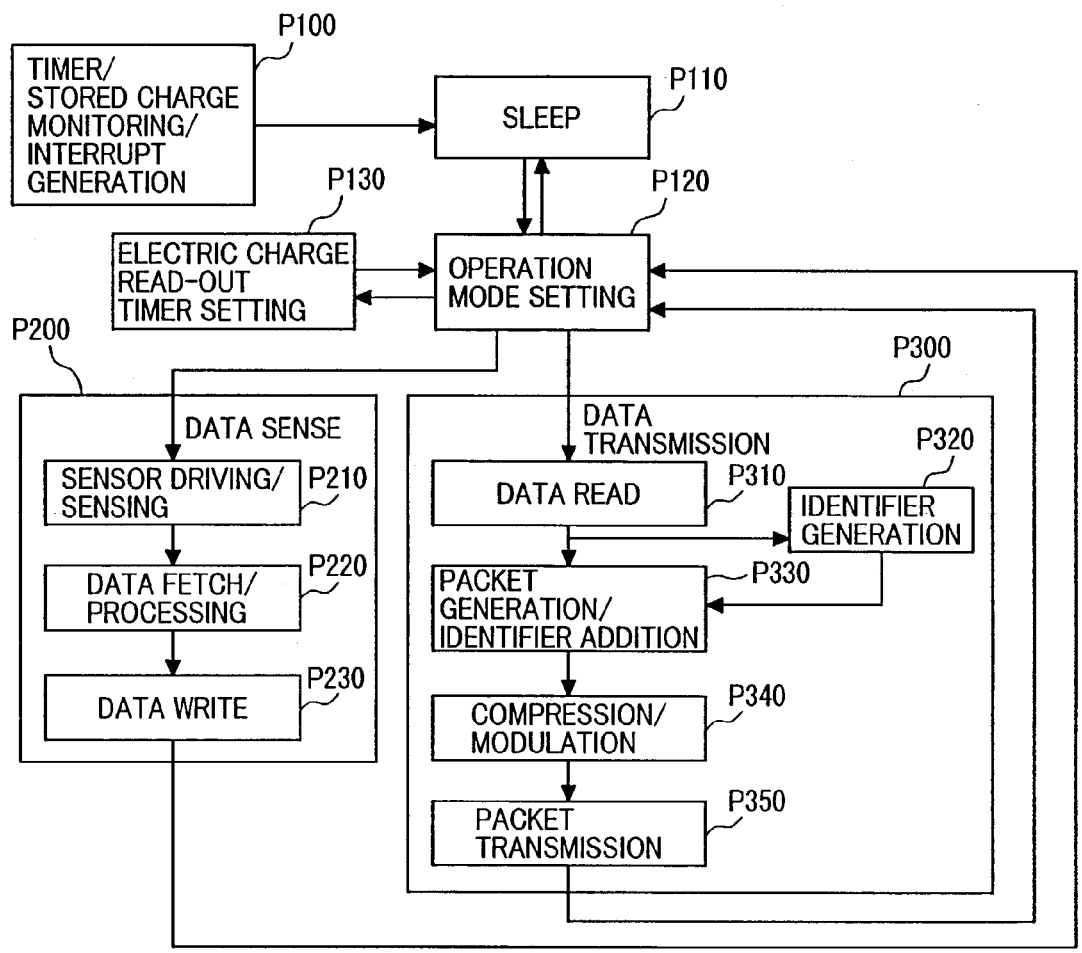
FIG. 7 is a functional block diagram of the operation of the sensor chip of the present invention.

To solve this problem, the present invention employs a low power consumption operation system that is formed by a capacitor C1, a timer TM1, a switch transistor TP1, an electric charge monitoring circuit CW1, and a power supply control circuit PC1. In other words, each circuit of the CHIP1 does not receive electric power continuously. Instead, generated power is accumulated in the capacitor C1. And, when a preset time in the timer TM1 is reached, or the electric charge monitoring circuit CW1 accumulates sufficient electric power, the switch transistor TP2 located in the power supply control circuit PC1 is turned on to supply the power to other circuits. This means that signal detection or communication with the outside is effected intermittently. FIG. 7 is a flowchart which shows the operations of this low power consumption operation system.

As shown in FIG. 7, the CPU1 is kept in the sleep state P110. The CPU1 goes into an operation state for executing processings in and after P120 in response to an interrupt from the timer TM1 or the electric charge monitoring circuit CW1. In the operation state, the CPU1 selects the next operation under the control of the program or according to the operation parameter stored in the memory MEM1. For example, if the operation parameter is specified for data detection, the CPU1 calls a data sense routine P200 and executes the sensor drive subroutine P210, the data fetch/process (compression, etc.) subroutine P220, and the data write subroutine P230 sequentially to obtain data from sensors, and it writes the obtained data in the memory. On the other hand, if the operation parameter is specified for data transmission, the CPU1 calls the data transmission routine P300 to execute the data read subroutine P310, the identifier creation subroutine P320, the packet creation subroutine P330, the compression/modulation subroutine P340, and the packet transmission subroutine P350 sequentially to transmit requested data.

Figure 8A:
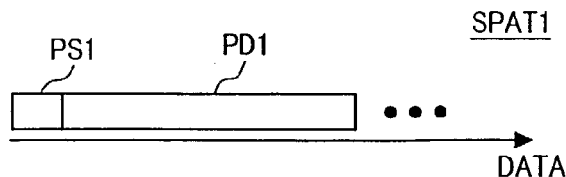
FIG. 8A is a diagram showing the data format of data to be transmitted to an external device from the sensor chip of the present invention.
Figure 8B:
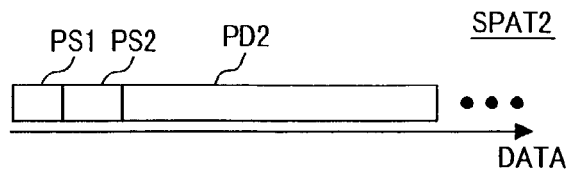
FIG. 8B is a diagram showing the data format of data to be transmitted to an external device from the sensor chip of the present invention.

As shown in FIG. 8A, detected data is transmitted in a format of packets (SPAT1), configured by an identifier (PS1) and data (PD1). Because an identifier is added to each data to be transmitted, for example, even when a plurality of the sensor chips of the present invention are used concurrently, it is possible for an external device, which is, for example, the MONITOR1 shown in FIG. 3, to identify each source sensor chip involved in the data transmission. The identifier PS1 may be information specific to a chip, such as a specific ID written in the non-volatile memory part of the memory MEM1, when the semiconductor integrated circuit CHIP1 is delivered. And, as shown in FIG. 8B, in addition to the identifier PS1, identification information (sensor type, PS2) that denotes which sensor of the sensor chip has transmitted the subject information may also be added to each data to be transmitted.

In the operation mode setting routine P120, in addition to the processings described above, other processings are performed; for example, data is read from the register CR1 that stores the charging state of the electric charge monitoring circuit CW1 or data is written in the time interval setting register TR1 of the timer TM1. Consequently, each of the processings can be specified in accordance with the state of the power generation chip CHIP2.

Figure 9:
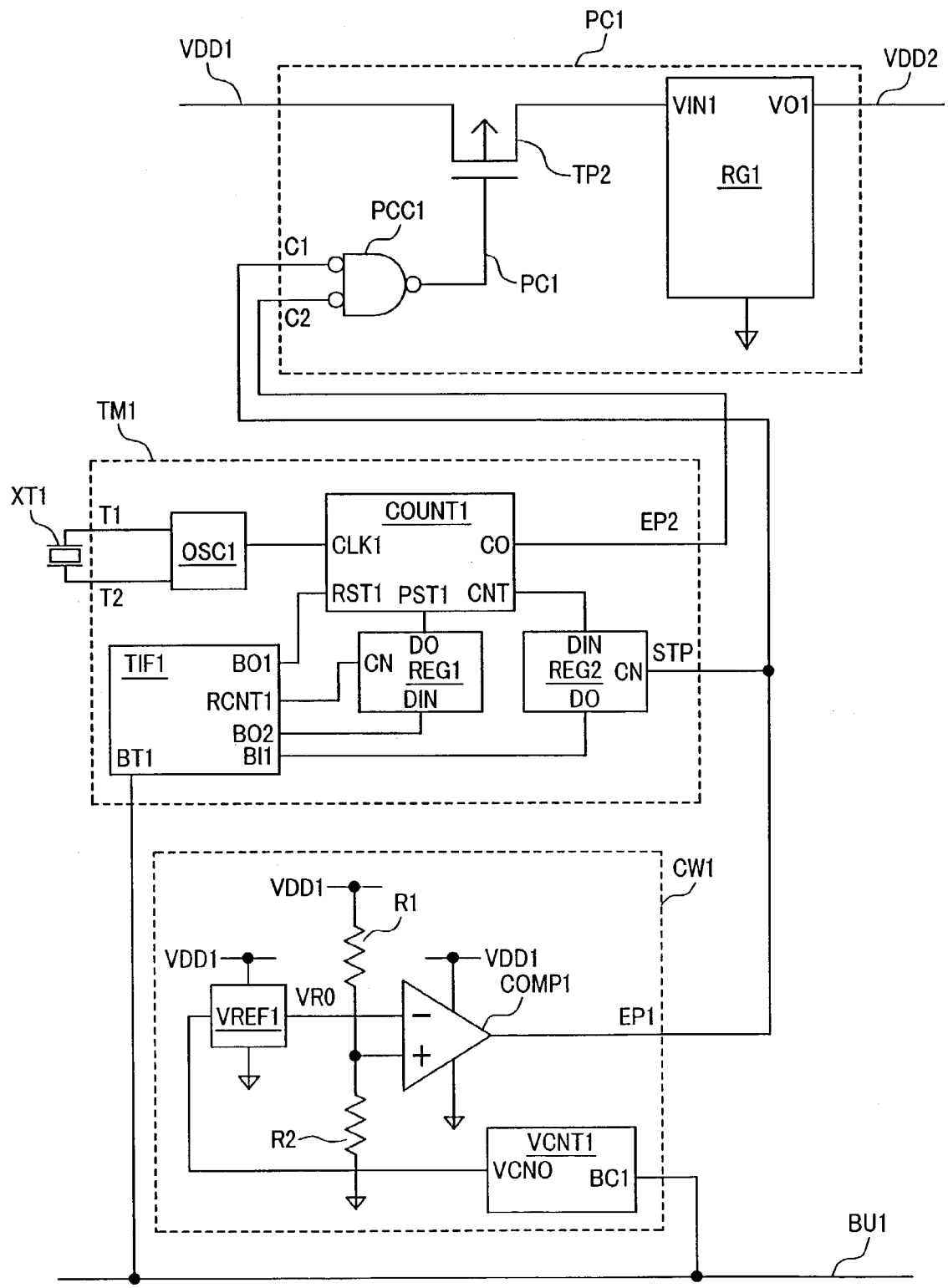
FIG. 9 is schematic diagram of a power supply control circuit, a timer circuit, and an electric charge monitoring circuit, that are all integrated in the sensor chip of the present invention.

FIG. 9 shows a block diagram that includes a power supply control circuit PC1, an electric charge monitoring circuit CW1, and a timer TM1, all of which are characteristic of the present invention. As shown in FIG. 9, the power supply control circuit PC1 is configured by a control logic circuit PCC1 and a switch transistor TP2. The output of the control logic PCC1 is driven into the low level, the switch transistor TP2 is turned on, and electric power is supplied to the VDD2 line, only when the levels of the signals EP1 and the EP2 that are received from the electric charge monitoring circuit CW1 or timer TM1 are low. Consequently, the memory MEM1, the high frequency transmission/reception circuit RF1, the A/D conversion circuit AD1, the sensor chip, and other circuits that are powered by the output VDD2 are actuated by this power supply.

The electric charge monitoring circuit CW1 is configured typically by resistors R1 and R2, a reference voltage generation circuit VREF1, and a voltage comparing circuit COMP1. The voltage comparing circuit COMP1 compares a voltage with the threshold voltage Vt1 given in accordance with the calculation result of the following expression. When VDD1>Vt1 is satisfied, the output EP1 is pulled down to the low level (=GND level).

[Expression 1]

$$Vt1 = VR0 \cdot (1 + R1/R2)$$

The value of this reference voltage VR0 can be changed from the CPU1 through a bus interface VCNT1. Because both VREF1 and COMP1 are powered continuously, resistors R1 and R2 are required to be designed as high resistors (a few tens of mega-ohms and over). Generally, those resistors R1 and R2 are formed in the CMOS process.

The timer TM1 is configured by an oscillation circuit OSC1, a preset counter COUNT1, a register REG1 for retaining a preset value of the COUNT1, a register REG2 for retaining a count value up to a predetermined voltage of the electric charge monitoring circuit CW1, and a bus interface TIF1 with the CPU1. The preset counter COUNT1 counts up to a preset value that is set in the register REG1 and outputs a low level EP2 signal. The values in these registers REG1 and REG2 are writable/readable in/from the CPU1 through the bus interface TIF1. The values in those registers REG1 and REG2 are set by the routine P130 shown in FIG. 7. Those circuits are not characteristic of the present invention, so they will not be described in detail here. And, because this timer circuit TM1 is also powered continuously, it is desirable that the power consumption should be reduced. To reduce this power consumption, the oscillation frequency of the oscillation circuit OSC1 should be suppressed to a low level. For example, if the oscillation frequency is set at 32 kHz or so, the power consumption of the timer TM1 is suppressed to 1 uA and under.

Figure 10:
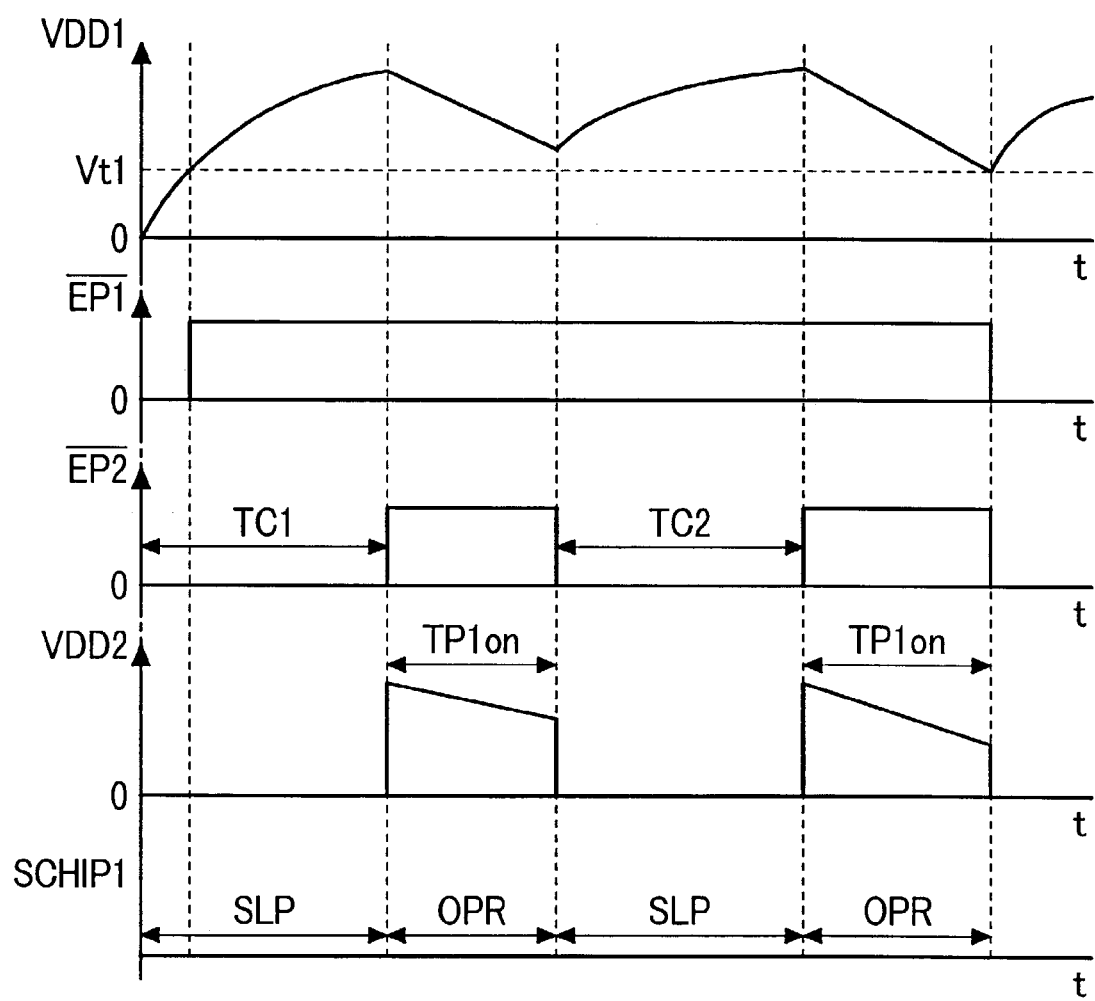
FIG. 10 is a graph of a low power consumption operation method realized by the power supply control circuit shown in FIG. 9.

FIG. 10 illustrates a way of reducing the power consumption significantly with use of the PC1, the CW1, and the TM1 according to the present invention. As shown in FIG. 10, most of the circuits of the semiconductor integrated circuit CHIP1 are usually in a sleep state (SLP); and, they function only for a short time intermittently (OPR). Because of such intermittent operations, the power consumption is reduced, as described above. For example, the capacitor C1 may be a capacitor of 1 uF or so. If the capacitor C1 is charged with 1V, the capacitor C1 can supply 1 u coulomb, that is, a current of 1 mA or so. In other words, if the charging voltage of the capacitor C1 is set at a few volts (usually 3V or so), data can be transmitted to the outside at a transmission power of 1 mW or so even when the RF power addition efficiency is 50%. On the other hand, if the power generated in the power generation chip is set at 0.1 mW and the capacitance of the capacitor C1 is set at 1 uF, it will take a time calculated by the following expression to charge the capacitor C1.

[Expression 2]

$$1\ \mu F/(0.1/3\ mA) = 30\ msec$$

Even if it takes 100 msec to charge the capacitor C1 with some time to spare, it is possible to drive the sensor chip more than ten times per second to detect or transmit data wirelessly at a high frequency. If the semiconductor device is used for a health care instrument, at the shortest, 10 times per second will be enough as a cycle for detecting data as required just like in this embodiment. (For example, the cycle of blood pulses of comparatively short duration is one second or so.) Consequently, even when a circuit operates at 0.1 sec (=100 msec) cycles intermittently like the present invention, no problem will arise from practical operations. In addition, the operation mode setting routine shown in FIG. 7 can set such intermittent operations, for example, so as to operate only once out of 10 times. If the number of the most power required data transmission times is reduced, the consumption of the electric charge accumulated in the capacitor C1 can further be reduced, the charging time is shortened, and the number of detection times is increased. The sensor chip of the present invention, in which a power supply control circuit that is characteristic of the present invention is combined with a very small power generator manufactured in the MEMS process, requires no battery to perform autonomous operations.

Figure 11:
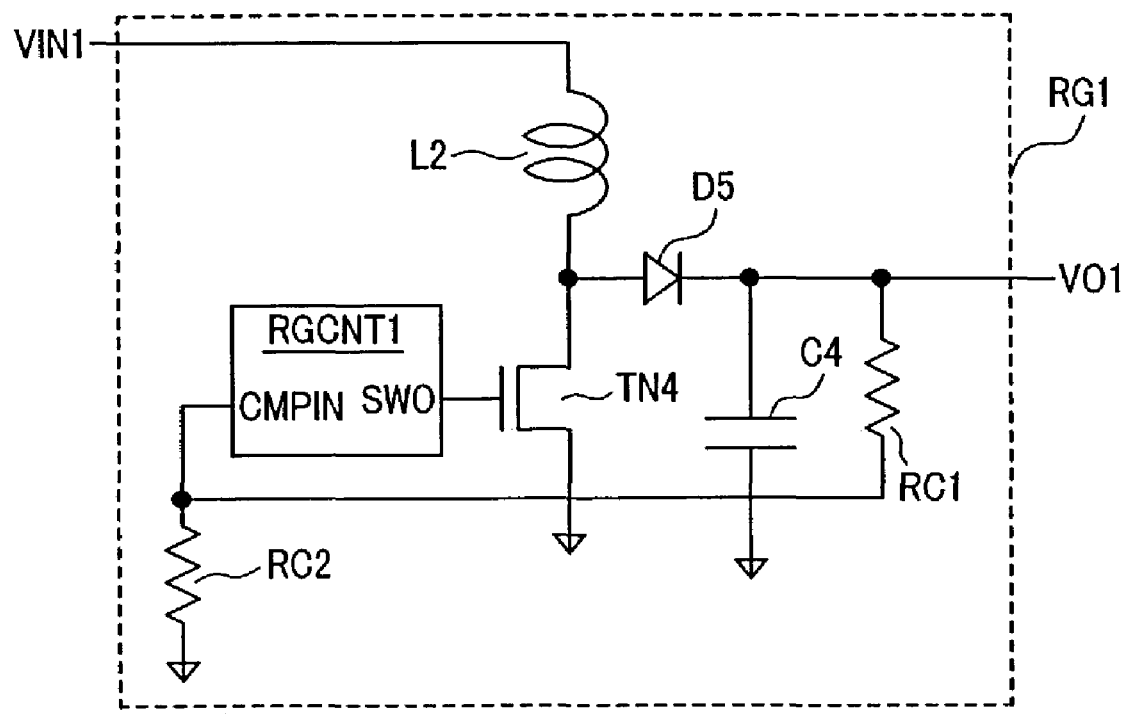
FIG. 11 is a schematic diagram of a regulator RG1 of the power supply control circuit shown in FIG. 9.

FIG. 11 shows a block diagram of a step-up regulator (RG1) that is usable in the power supply control circuit to supply a higher supply voltage. This regulator is not necessarily required, however. For example, the regulator may be omitted if a proper voltage is output from the power generation chip.

Figure 12A:
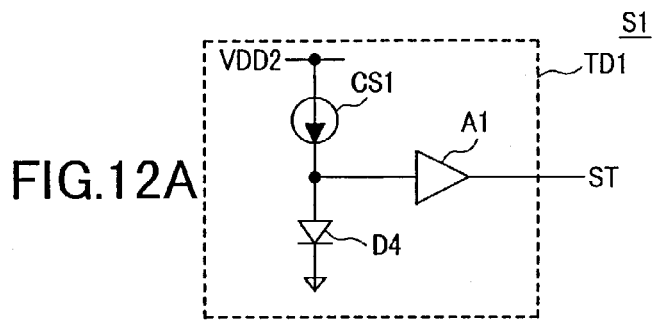
FIG. 12A is a schematic diagram of a temperature sensor integrated in the sensor chip of the present invention.

FIGS. 12A to 12D are diagrams of various types of sensors formed in the first semiconductor integrated circuit in the sensor chip of the present invention. Hereinafter, the configuration of each of the sensors will be described. FIG. 12A shows a temperature sensor configured by a diode D4, a constant current circuit CS1, and an amplifier A1. The amplifier A1 measures a variation (temperature coefficient: up to 2 mV/° C.) of the forward voltage of the diode D4 caused by temperature; and, the result is read by the microprocessor CPU1 through the A/D conversion circuit (to be described later), and then it is corrected as needed to measure the temperature. The amplifier, the constant current circuit, and other circuits described here are not characteristic of the present invention, so that a detailed description thereof will be omitted here. This sensor chip is very small (typically, 5 mm square or under) and the thermal capacity of the chip itself is negligible when compared with, for example, that of the human body. In addition, the power consumption of the sensor chip is very low and the heat release of the chip itself is negligible. Consequently, this sensor chip, when it is set in contact with a human body, as shown in FIG. 3, can measure the bodily temperature accurately. The configuration of the temperature sensor shown in FIG. 12 is just an example; the configuration may be modified freely.

Figure 12B:
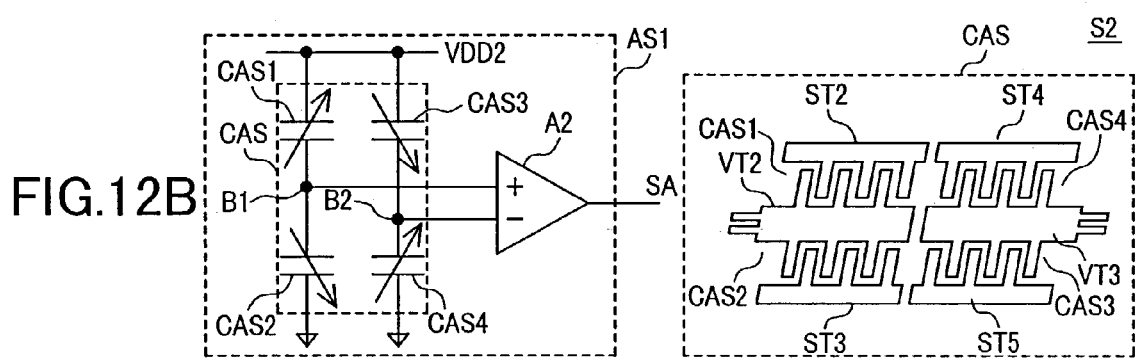
FIG. 12B is a schematic diagram of an acceleration sensor integrated in the sensor chip of the present invention.

On the other hand, the acceleration sensor, as shown in FIG. 12B, is configured by variable capacitors CAS1 to CAS4, that are manufactured in the MEMS process, and a differential amplifier A2. These variable capacitors are basically the same in structure as the power generation capacitor CM1 that is formed in the power generation chip CHIP2 described above. Just like the capacitor CM1 shown in FIG. 1, the capacitance of each of the capacitors CAS1 to CAS4 varies as the distances between the movable electrodes and each fixed electrodes are changed by the inertia force generated by acceleration. For example, in FIG. 12B, if an acceleration occurs in the vertical direction, the variable capacitors VT2 and VT3 move upward. Consequently, the capacitance values of the capacitor CAS1 and the capacitor CAS2 increase, while the capacitance values of the capacitor CAS2 and the capacitor CAS4 decrease. The potential of the point B1 thus comes to rise, while the potential of the point B2 comes to fall. As a result, the output potential of the differential amplifier A2 rises, whereby the acceleration is detected.

Unlike the variable capacitor CM1 that is used in the power generation chip, relative capacitance changes are important for the acceleration sensor. This is why the acceleration sensor is not required to be so large in capacity, and, accordingly, the sensor can be integrated together with the CPU and other circuits in the same semiconductor integrated circuit. And, the potential difference to be detected is not linear to the added acceleration. In some cases, therefore, the detected potential difference, after it is loaded into the microprocessor CPU1 through the A/D conversion circuit (to be described later), must be corrected by software. In this connection, a correction table should preferably be prepared in the memory MEM1 beforehand.

This acceleration sensor is usable, for example, to determine various actions of the user (sitting, walking, and running). If two acceleration sensors are used that are arranged in two directions that are orthogonal to each other at 90 degrees (X and Y directions), a two-dimensional acceleration can be detected, whereby the direction in which the user is moving can be determined. The acceleration sensor is also usable to check simply to see if there are vibrations, such as produced by the heartbeats of the user.

Figure 12C:
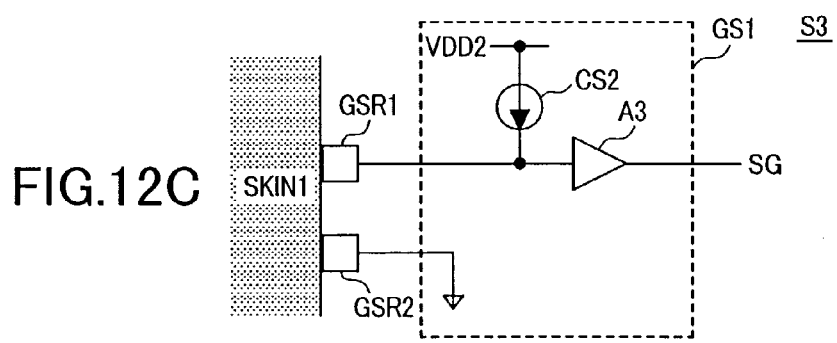
FIG. 12C is a schematic diagram of an impedance sensor integrated in the sensor chip of the present invention.

FIG. 12C shows a block diagram of an impedance sensor. The impedance sensor is configured by a constant current source CS2 and an amplifier A3, and it is used to measure a voltage drop between the electrodes GSR1 and GSR2 provided outside the semiconductor integrated circuit. The measured voltage drop is divided by the current value set in the constant current source GS2 so as to measure the electrical impedance between these two electrodes. For example, the impedance sensor measures the electrical impedance of the user's skin SIN1. If the measured electrical impedance is processed by the microprocessor CPU 1, the Galvanic Skin Reflex is found, thereby the user's feelings (angry, delighted, sad, etc.) or the user's stress can be determined.

Figure 12D:
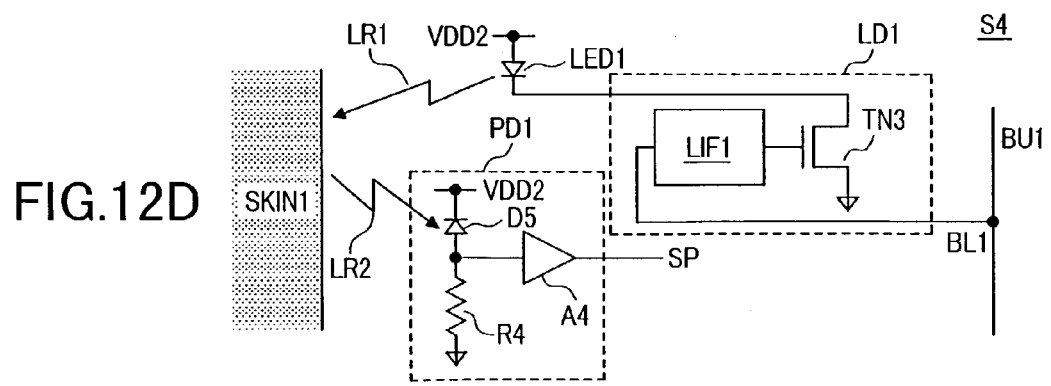
FIG. 12D is a schematic diagram of a blood pulse sensor integrated in the sensor chip of the present invention.

FIG. 12D shows a block diagram of a blood pulse sensor. This blood pulse sensor is configured by a photo-sensor PD1 consisting of a photo-diode D5, a load resistor R4, and an amplifier A4; a red/infrared ray LED mounted on the substrate and used as a light source of the photo-sensor PD1; and a drive circuit LD1 consisting of a bus interface LIFI and a drive transistor TN3 for the LED1. In this blood pulse sensor, the transistor TN3 is turned on according to a control signal from the microprocessor CPU1 through the bus BU1 only at the time of measurement, thereby the LED1 comes on to irradiate a red or infrared ray onto the user's skin SKIN1. The photo-diode D5 receives the reflection/scattered light (LR2) of the irradiated light (LR1), as well as other light. The received light is amplified in the amplifier A4, and then it is transferred to the microprocessor CPU1 through the A/D conversion circuit so that the intensity of the light is measured therein. As a result, the transition (=blood pulses) of the red/infrared ray attenuation is measured according to the blood flow rate. Usually, an LED needs at least a driving current of 1 mA or so to emit a red/infrared ray at enough intensity. This is why the very low power consumption operation method that is characteristic of the present invention is indispensable to drive this blood pulse sensor intermittently by an electric charge accumulated in the capacitor C1, just like the high frequency transmission/reception circuit.

This blood pulse sensor is used to carry out measurements on the basis of the principle that the hemoglobin in the blood absorbs red or infrared rays, thereby how much hemoglobin flows in the blood can be determined by measuring the absorbed amount (=light attenuation amount). And, it is known that the light absorbing characteristics of the hemoglobin vary between when the hemoglobin sucks oxygen and when the hemoglobin sucks no oxygen. Therefore, it is well known that if the absorption is measured in both the red ray and the infrared ray ranges, the degree of oxygen saturation in the blood can be estimated with a simple expression. And, this degree of oxygen saturation can be used to estimate the blood sugar level and other values of the user. In addition, the sensor chip of the present invention can measure this degree of oxygen saturation in a time division manner with the use of two red or infrared ray LEDs. The blood pulse cycle depends deeply on whether the user is nervous or relaxed. The microprocessor CPU1 in which this sensor chip is mounted can be used to determine such blood pulses of the user, as well as the health condition, feelings, etc. of the user.

The outputs of the sensors described above are all analog values. To fetch the analog values into a CPU and transmit them to an external device wirelessly through an RF circuit, the values must be converted to digital values. To meet this requirement, an A/D converter is connected to the output of each of the sensors to perform such analog-to-digital conversion. Providing the sensor chip with a plurality of A/D conversion circuits in such a way, however, should be avoided so as to not expand the chip area and increase the power consumption. It is recommended to use only one A/D conversion circuit as shown in FIG. 13 to realize such analog-to-digital conversion collectively.

Figure 13:
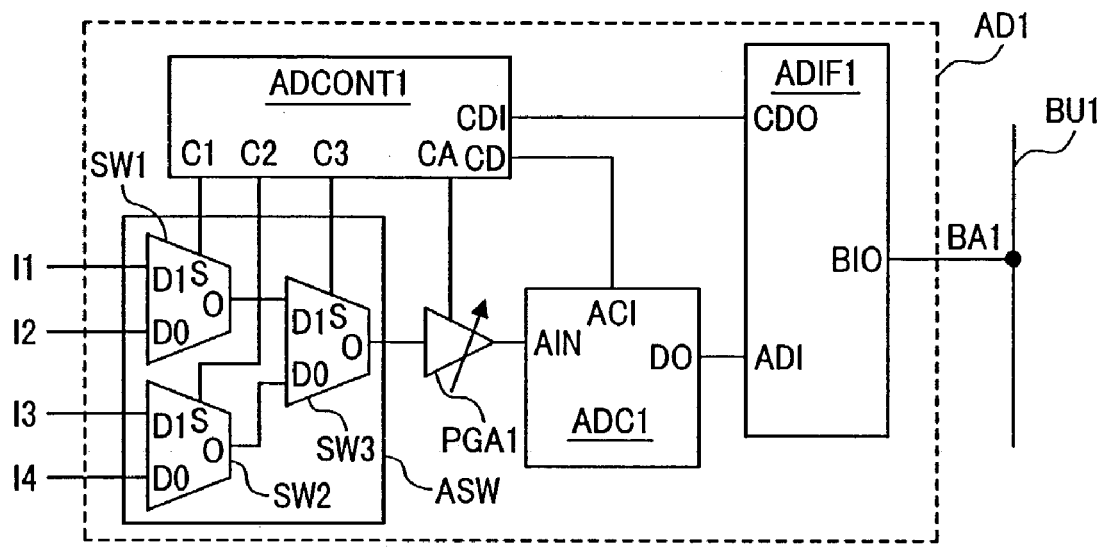
FIG. 13 is a block diagram of an A/D conversion circuit provided with a selection function, which is included in the sensor chip of the present invention.

As shown in FIG. 13, the A/D conversion circuit (AD1) is configured by a bus interface circuit ADIF1, an ADC1 that forms the main element of the A/D conversion circuit, an input switch ASW composed of switch elements SW1 to SW3, a programmable gain control amplifier PGA1, and an A/D conversion control circuit ADCONT1 for setting the operation parameters for those circuits. The ASW and the PGA1 that are characteristic of the present invention are used to set operation parameters in the control circuit ADCONT1 according to the control commands received from the CPU1 through the bus BU1.

For example, in the case of temperature measurement, the control register located in the ADCOUNT1 is set under the control of the CPU1 through the bus BU1 so that the input selection switch ASW selects I1 (SW1: D1, SW3: D1) and the gain set by the programmable gain control amplifier PGA1 becomes a proper gain for the temperature sensor prior to the measurement. According to this setting, the output ST of the temperature sensor is fetched into the A/D converter through the PGA1 and is converted to a digital value, and then it is transferred to the CPU through the bus interface ADIF1. Similarly, to read the output of another sensor, a proper gain for the target sensor, as well as the set value of the input selection switch are written in the control register located in the ADCONT1 to drive the ADC1. And, according to such a configuration, the chip size and the power consumption are prevented from increasing respectively.

Figure 14:
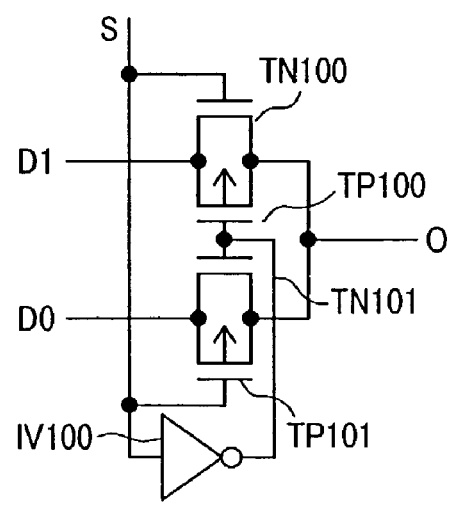
FIG. 14 is a schematic diagram of a multiplexer of the A/D conversion circuit shown in FIG. 13.

In this connection, each of the switch elements SW1 to SW3 of the input selection switch must pass analog signals with no loss. For example, a path transistor type switch configured by PMOS and NMOS transistors, as shown in FIG. 14, is usable as such a switch. In this sensor chip, the AND conversion circuit ADC1 may be replaced with a slower one, since the information to be detected is limited only to that obtainable from the living body.

Figure 15:
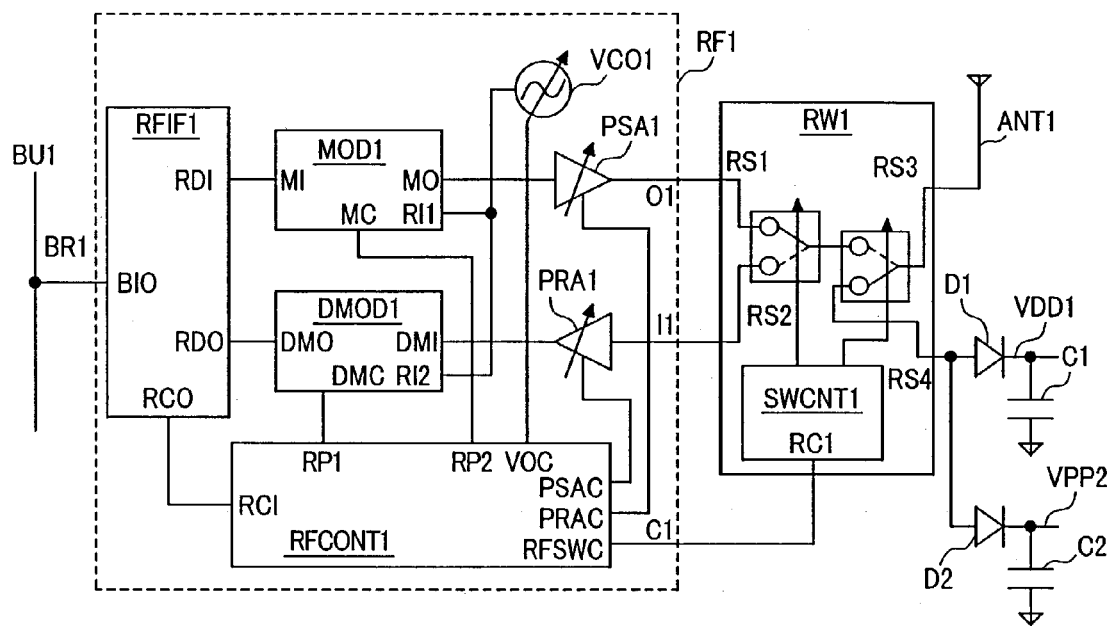
FIG. 15 is block diagram of a high frequency transmission/reception circuit and a high frequency switch that are integrated in the sensor chip of the present invention.

FIG. 15 shows a block diagram of a high frequency switch RW1 for switching between connections to the high frequency transmission/reception circuit RF1 for transmitting detected information to an external device, as well as between the circuit RF1 and an antenna. The high frequency transmission/reception circuit RF1 is configured by a bus interface RFIF1, a modulation circuit MOD1 that is used for transmitting signals, a transmission amplifier PSA1, a demodulation circuit DMOD1 that is used for receiving signals, a receiving amplifier PRA1, and a control circuit RFCONT1 for controlling the operation parameters of those circuits according to the content of the control register, which is set under the control of the CPU1 through the bus interface RFIF1. Because those circuits are not characteristic of the present invention, no description will be provided for them here. When transmitting data, however, the CPU1 sets the control register located in the control circuit RFCONT1 in the transmission mode and transmits the data to the modulator MOD1 through the bus interface. The modulator MOD1 thus modulates the carrier wave generated by the oscillation circuit VC01 on the basis of the received data. The modulation method used at this time may be any of PSK (Phase Shift Keying), QAM (Quadrature Amplitude Modulation), etc. The modulation method is not a characteristic of the present invention, so no description will be made for the method here. The carrier wave that is modulated as described above is then amplified by the transmission amplifier PSA1, in which the gain is controlled by the control circuit RFCONT1, and then it is transmitted to the high frequency selection switch RW1.

As disclosed in the above-referenced document 9, the high frequency switch RW1 is usually configured by a micro-contact or the like formed on the surface of the target semiconductor chip in the MEMS process, just like the semiconductor elements of each PIN diode, as well as the CM1 and the CAS. The switch RW1 switches among destinations of each RF signal by controlling the bias voltage at a PIN diode or MEMS micro-contact according to a control signal obtained from a control terminal RC1. More specifically, the switch RW1 is set so that the connection between the line RS1 and the line RS3 is validated through the RC1 terminal according to the value set in the setting register located in the control circuit RFCONT1 through the CPU1 at the time of transmission. Similarly, at the time of reception, the connection between the line RS3 and the line RS2 is validated, thereby the demodulation circuit DMOD1 demodulates each high frequency signal received from the antenna. The CPU1 can read the demodulated signal through the bus interface RFIF1. The above-described receiving function is also usable for setting the operation parameters to be stored in the memory MEM1. For example, the receiving function is usable to change the starting interval for sensor chip detection, as well as the operation parameters of each sensor (amplifier's gain, etc.).

The switch RW1 is set to connect the line RS3 and the line RS4 to each other electrically at any event other than data transmission or reception. Consequently, high frequency electrical power received from an antenna is accumulated in the capacitor C2, so that the power generation chip is charged with the accumulated power through the rectifier D2. The capacitor C1 that drives this sensor chip intermittently through the rectifier D1 is also charged with the accumulated power similar to the capacitor C2. The sensor chip of the present invention receives electric power from an external device through an antenna in this way.

As described above, RF transmission requires a comparatively large electric power. In such a case, therefore, data is transmitted to an external health care instrument (ex., MONITOR1) only once a day, while the data is usually detected and stored in the memory. Thus, the power consumption is greatly reduced.

Figure 16:
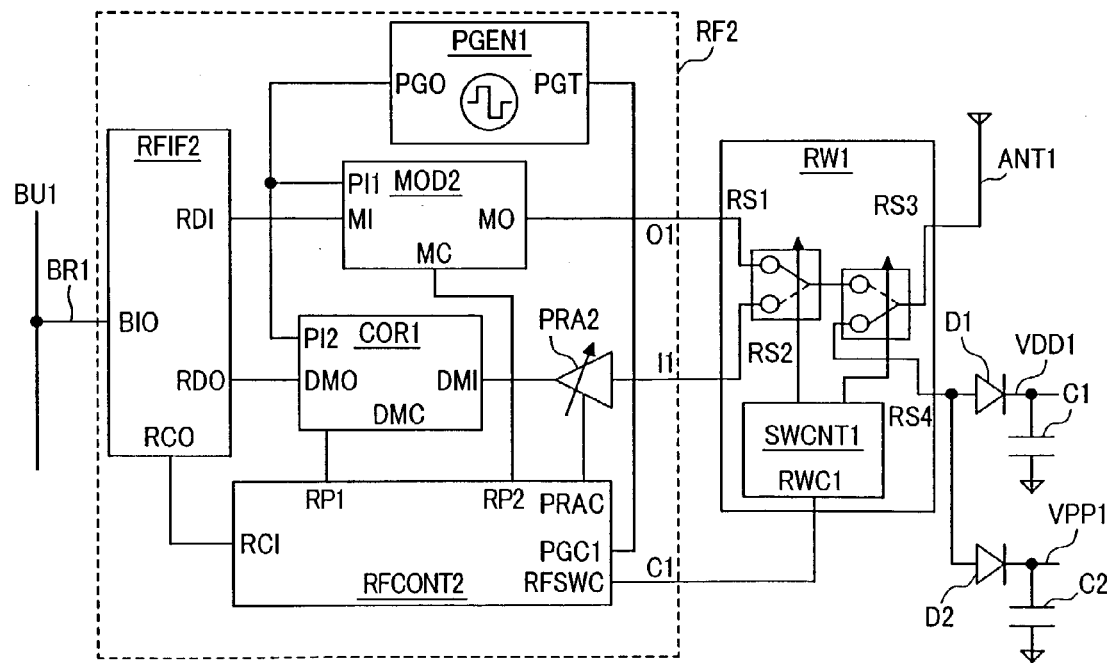
FIG. 16 is a block diagram of the high frequency transmission/reception circuit included in the sensor chip of the present invention.

Furthermore, as disclosed in the above-referenced document 10, the UWB (Ultra Wide Band) in which an ultra-wide band radio communication method is employed, can be used to reduce the power consumption similarly. Unlike the PSK, the ASK, etc. methods described above, however, high frequency pulse signals themselves are modulated to transmit data in the UWB. For example, when "1" is set for the data to be transmitted, pulses are transmitted. When "0" is set for the data, pulses are delayed by 100 ps, then transmitted to modulate the pulse strings with use of the transmitted data. Consequently, as shown in FIG. 16, the high frequency transmission/reception circuit RF2 may be configured with only a pulse generator PGEN1 for generating pulses and a modulator MOD2 for controlling whether to transmit the pulses. In other words, the transmission amplifier required indispensably in such a narrow band communication method as the PSK, the QAM, or the like methods, as employed in the example shown in FIG. 15, may be omitted, thereby the high frequency transmission/reception circuit is reduced in scale. As a result, the chip manufacturing cost, as well as the power consumption of the sensor chip, are reduced.

Furthermore, in using the UWB, the RF transmission power can be suppressed, while requests are made only for comparatively short distance communications. This is because such a UWB sensor chip, for example, when it is stuck on a user's arm, is merely required to transmit data to a portable health care instrument carried in a user's breast pocket. (For example, the communication distance in such a case will be a few tens of centimeters.) Consequently, the RF transmission power may be set, for example, at a few tens of micron-watts. The UWB will thus be employed more favorably as a radio communication method for the sensor chip of the present invention.

The UWB, however, needs a correlator (COR1 shown in FIG. 16) to receive data as described above. This correlator usually correlates received pulse strings with pulse strings supplied from the pulse generator located in the receiving chip. More specifically, the correlator is a circuit for detecting if a pulse string is delayed by 100 ps to reproduce target data. Generally, this correlator uses a plurality of A/D conversions, thereby the correlator circuit becomes complicated and large in scale. Because of such characteristics, the correlator might lose the UWS advantage that "the transmitter can be simplified".

Figure 17:
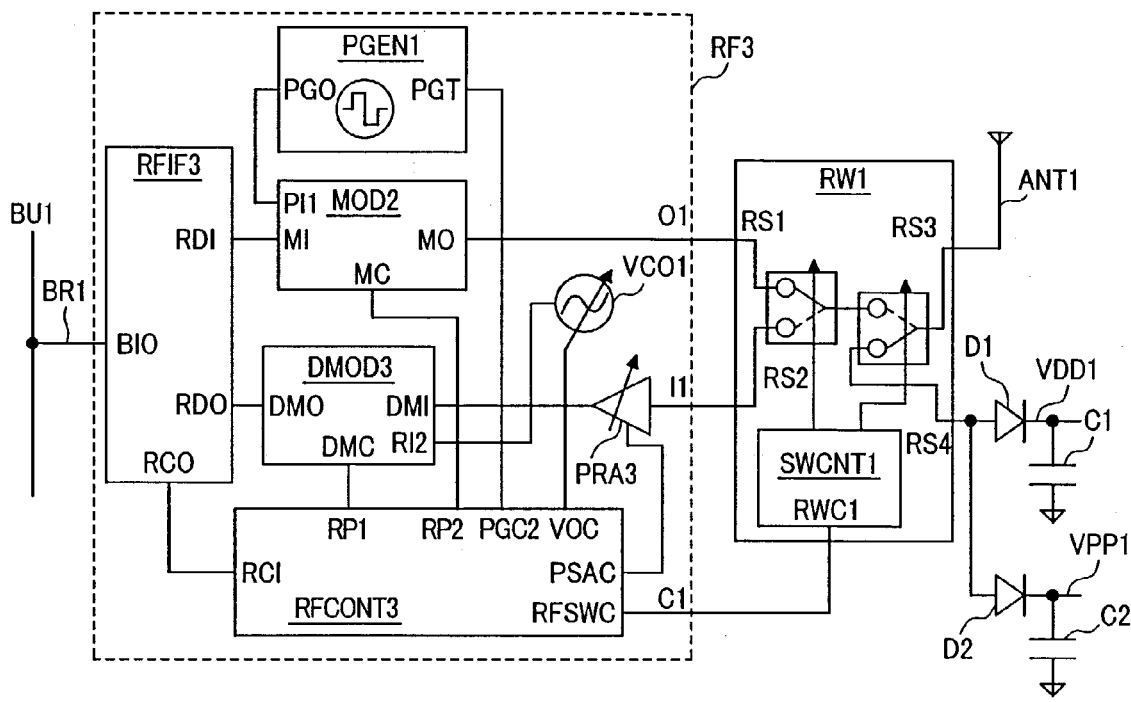
FIG. 17 is a block diagram of the high frequency transmission/reception circuit included in the sensor chip of the present invention.

To avoid this, a high frequency transmission/reception circuit RF3, that is configured as a hybrid, as shown in FIG. 17, is used. In this hybrid configuration, the UWB communication method described with reference to FIG. 16 is used only for transmission (with use of the pulse generator PGEN1 and the modulator MOD2). On the other hand, a narrow band communication method, such as the PSK, the QAM, or the like, as described with reference to FIG. 15, is used for receiving (with use of the receiving amplifier PRA3, the oscillator VC01, and the demodulator DMO3). The hybrid configuration eliminates a complicated correlator circuit that has been indispensable for reception in the USB and reduces the scale of the circuit RF3 and the power consumption (RF transmission power) of the circuit RF3. The configuration of the high frequency transmission/reception circuit RF3 will thus be effective to achieve the objects of the present invention.

Figure 18:
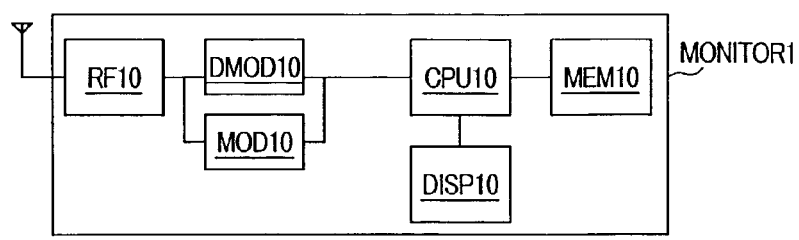
FIG. 18 is a block diagram of a portable health care monitor used for the health care instrument shown in FIG. 3.

FIG. 18 shows a block diagram of a health care instrument that uses the sensor chip of the present invention as described above. In FIG. 18, a health monitor MONITOR1 (as may be employed in the system of FIG. 3) is usually configured by a high frequency transmission/reception circuit (RF10), a modulation/demodulation circuit (MOD10, DMOD10), a processor (CPU10), a memory (MEM10), and a display unit (DISP10). Those circuits are not characteristic of the present invention, so no detailed description thereof will be made here.

Figures 19, 20:
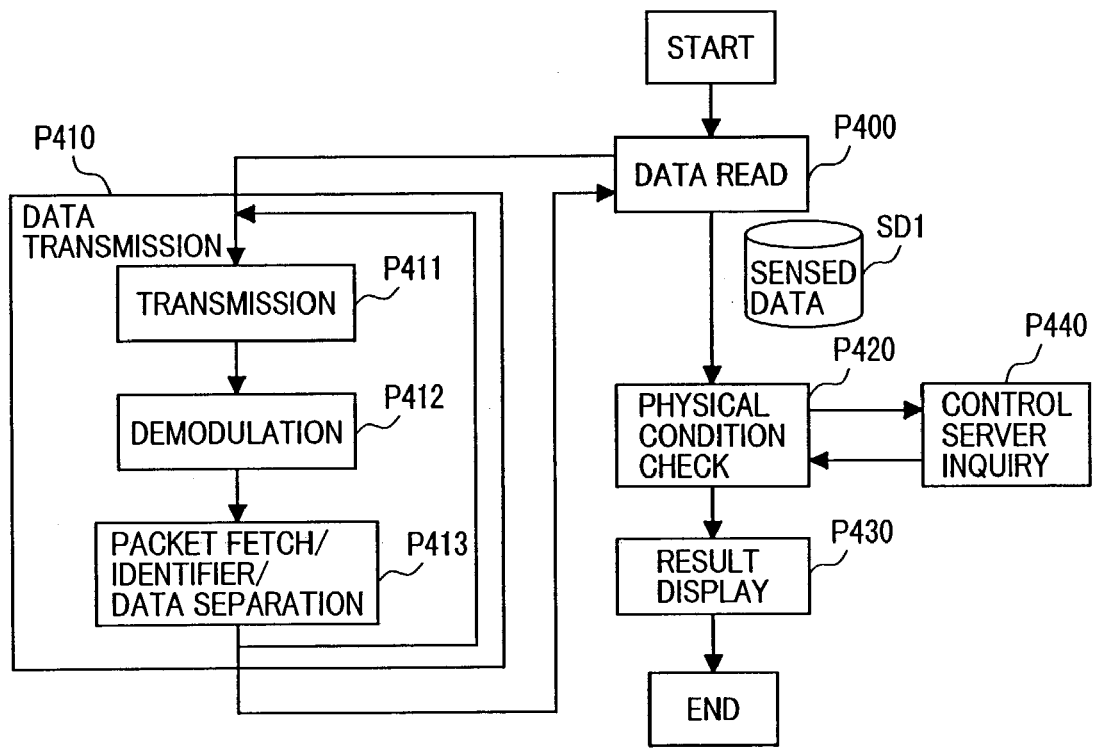
FIG. 19 is a flowchart of the processings in the portable health monitor shown in FIG. 18.
FIG. 20 is a table showing an example of packet data to be transmitted to an external device from the sensor chip of the present invention.

FIG. 19 shows a flowchart of the operation of the MONITOR1. At first, a data read routine (P400) and a data reception routine (P410 to 413) are started, so that the RF10 receives a signal from a sensor chip through a wireless connection device WL1 and the DMOD10 demodulates the signal to take out sense data (SD1).

FIG. 20 shows an example of the structure of the sense data detected and demodulated as described above. As shown in FIG. 20, the sense data SD1 is configured by a chip ID (CID), a sensor ID (SID), and data (DATA) so that it is possible to identify which sensor of which chip is a source for data transmission. The condition diagnosis routine (P420) diagnoses the user's health condition and the result display routine (P430) displays the diagnosis result on the DISP10. As shown in FIGS. 3 and 19, the condition diagnosis routine P420 also enables the sensor chip to be connected to a health information data base server (DSV1, DB1) that is connected to a wide range network (WAN1), such as a portable telephone network or the Internet, through the wireless connection device WL2 so as to make it possible to refer to the health condition information and obtain more accurate diagnosis information.

Figure 21A:
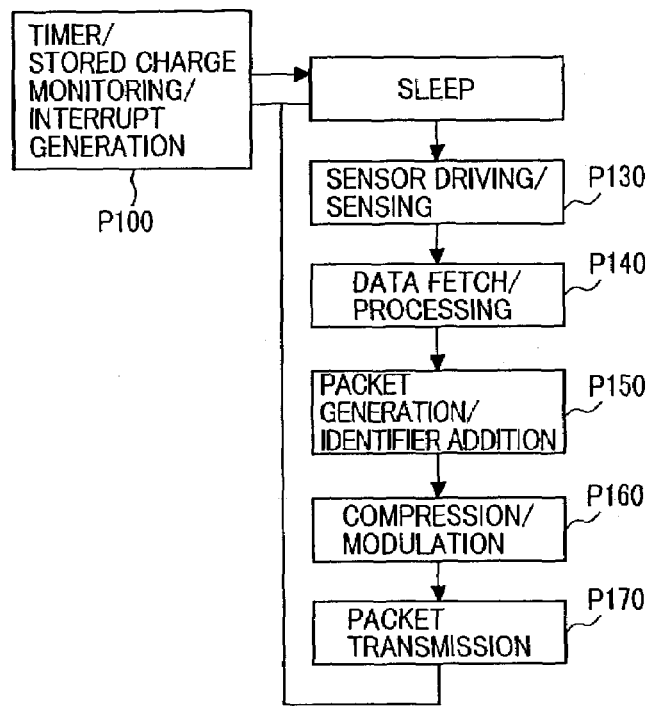
FIG. 21A is a functional diagram showing another example of the detected data transmission method employed for the sensor chip of the present invention.
Figure 21B:
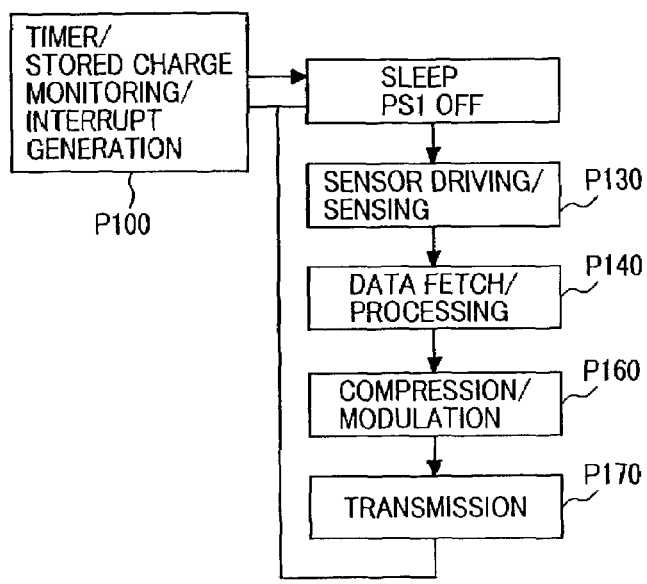
FIG. 21B is a functional diagram showing another example of the detected data transmission method employed for the sensor chip of the present invention.

Furthermore, as shown in FIGS. 21A and 21B, the transmission/reception procedure of the sensor chip can be further simplified. For example, FIG. 21A shows an example of transmission of detected data without storing it in any memory. FIG. 21B shows an example of transmitting data without adding identification data, such as a chip ID, etc., to the data. When the transmission/reception procedure is simplified in such a way, for example, the number of the CPU functions can be reduced, whereby the memory is reduced in capacity and the sensor chip is reduced both in area and power consumption. Such a simplified configuration can be adopted for some application purposes.

As described above, the use of the sensor chip of the present invention makes it possible to realize a compact and light-weight health care instrument that is free of both maintenance and battery replacement. Furthermore, the use of the sensor chip of the present invention enables the user to put on the health care instrument for a long time to obtain data intermittently. The sensor chip in which various types of sensors are built transmits detected data to the outside wirelessly. Consequently, no wire is used for connecting those sensors to the instrument body. This is why the instrument is very easy to operate, and the user can continue to receive his/her body data for a long time intermittently while he/she carries the sensor chip on his/her skin with no load. In addition, because the sensor chip is formed with semiconductor integrated circuits, mass production is possible for the chip. The manufacturing cost is thus reduced.

Second Embodiment

Figure 22:
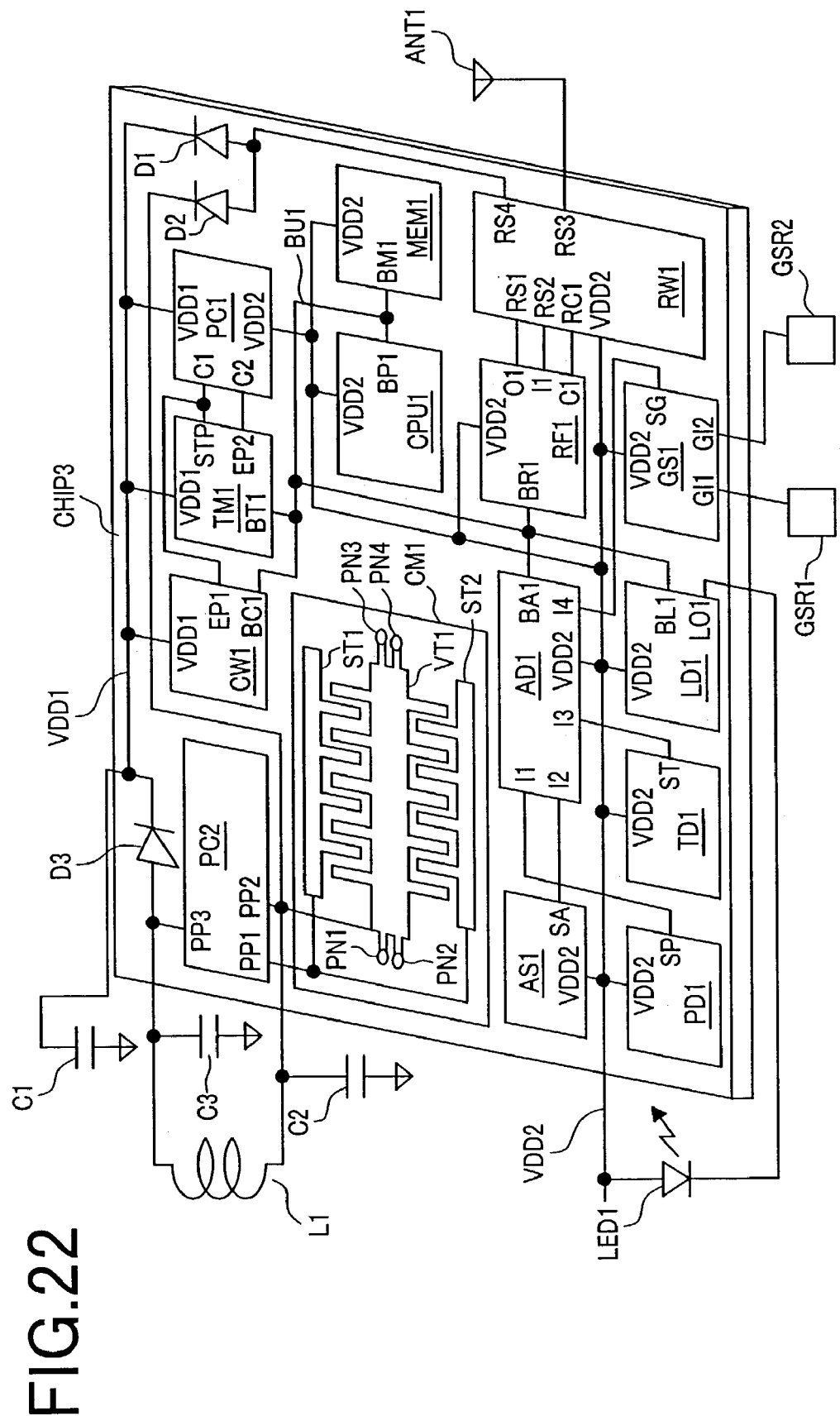
FIG. 22 is a diagrammatic perspective view showing an example of a sensor chip according to a second embodiment and configured by one semiconductor integrated circuit in which parts other than a capacitor, an inductor, and an LED are integrated.

In the first embodiment, the MCP configuration is employed for the sensor chip of the present invention. On the other hand, the MEMS process is compatible with the semiconductor process, so that the MEMS variable capacitor can be integrated with other circuits, such as the sensors, the microprocessor, etc. on one chip. FIG. 22 shows a sensor chip in which the MEMS variable capacitor is integrated together with such other circuits as sensors, a microprocessor, etc. The sensor chip can also be reduced in size even in such a configuration. However, the MEMS variable capacitor is required to have a comparatively large area. If the sensor chip has a configuration as shown in FIG. 22 and a large MEMS variable capacitor is used, therefore, it is difficult to reduce the sensor chip in size.

Figure 23A:
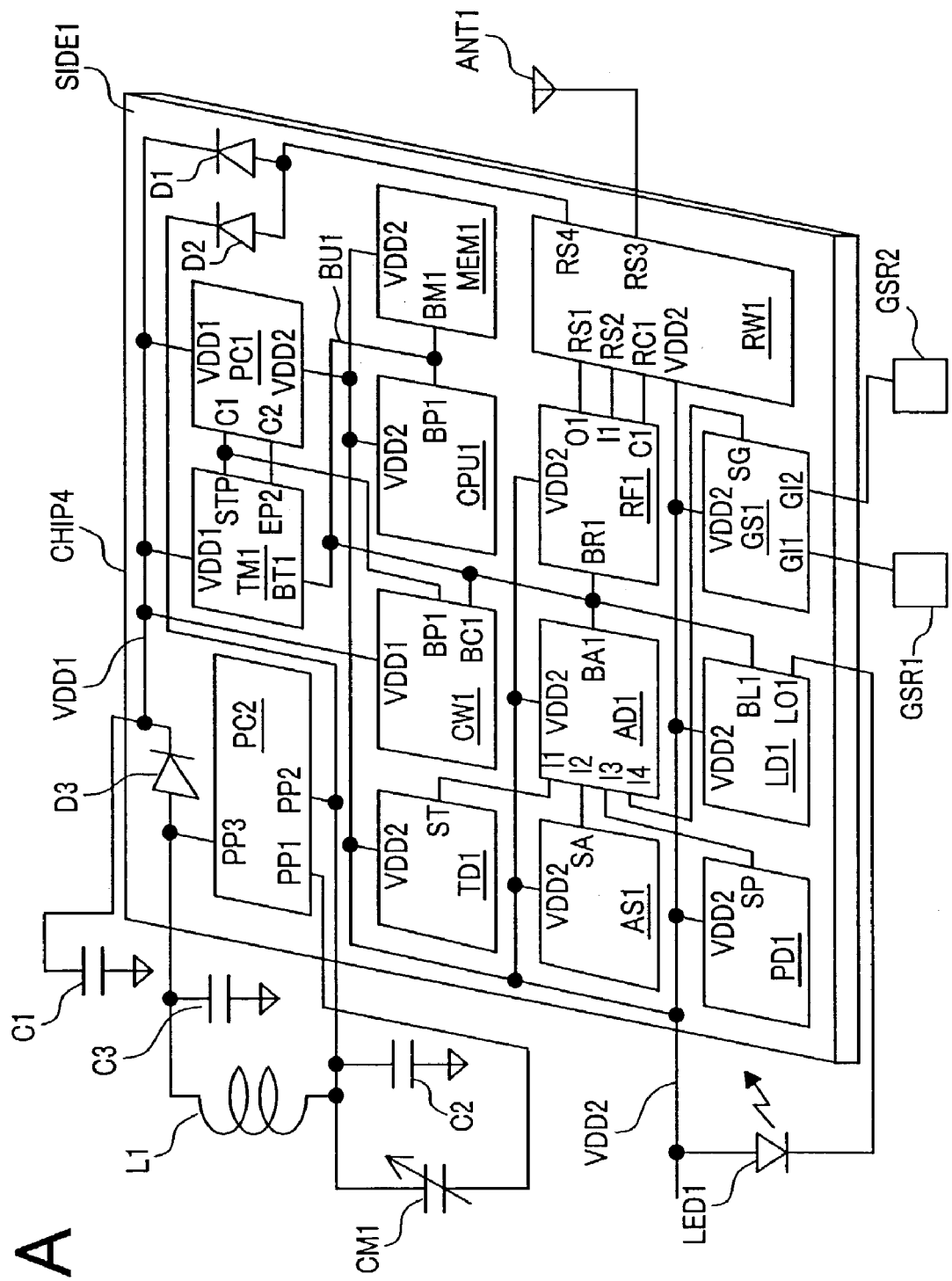
FIG. 23A is a diagrammatic perspective view showing another example of the sensor chip according to the second embodiment and configured by one semiconductor integrated circuit in which parts other than a capacitor, an inductor, and an LED are integrated.
Figure 23B:
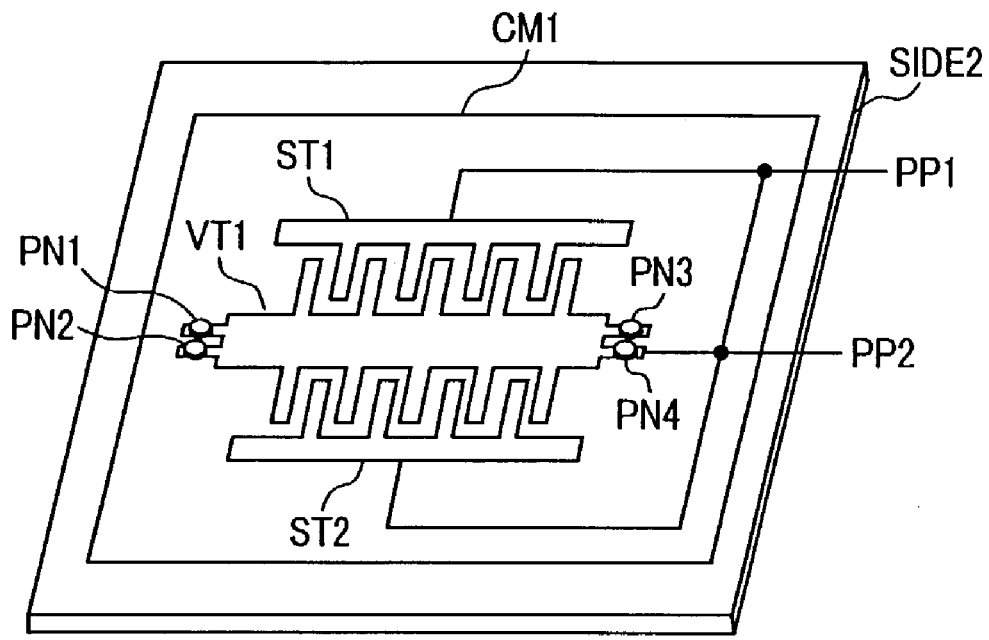
FIG. 23B is a diagrammatic perspective view showing another example of the sensor chip according to the second embodiment and configured by one semiconductor integrated circuit in which parts other than a capacitor, an inductor, and an LED are integrated.
Figure 23C:
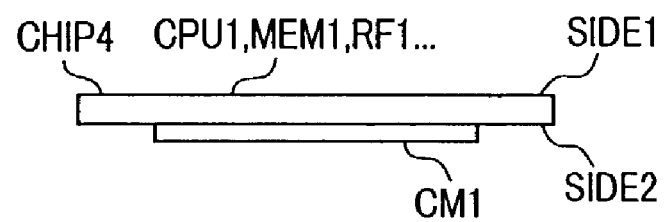
FIG. 23C is a diagram showing another example of the sensor chip according to the second embodiment and configured by one semiconductor integrated circuit in which parts other than a capacitor, an inductor, and an LED are integrated.

FIG. 23A through FIG. 23C show a favorable configuration of such a sensor chip to reduce its size. In FIGS. 23A through 23C, the configurations of the PC1, PC2, and CPU1 circuits are the same as those in the first embodiment. In this sensor chip, the MEMS variable capacitor is formed on the back side (SIDE2) of the chip. In other words, the sensor chip is split-structured, so that the circuits, such as the sensors and the microprocessor, are formed on the front side (SIDE1), while the MEMS variable capacitor is formed on the back side (SIDE2) of the chip. With such a structure, the sensor chip is even further reduced in size compared to the sensor chip (FIG. 22) in which both of the semiconductor circuits and the MEMS variable capacitor are formed on the same surface.

Furthermore, instead of the method of forming the MEMS variable capacitor on the back side (SIDE2) of the chip, as described above, another method may be employed. More specifically, a MEMS variable capacitor is formed on a chip beforehand, and the chip and another chip on which other circuits, such as the sensors, the microprocessor, etc., are formed are stuck on each other at their back sides. Thus, the sensor chip formed in such a way can be reduced in size roughly up to that of the sensor chip formed by the above-described method.

Furthermore, although not shown here, the MEMS variable capacitor may be formed on a passivation film that covers the surface (SIDE1) of the chip in which the sensors, the microprocessor, etc. are integrated. This method also realizes a more compact sensor chip as described above.

Third Embodiment

In the first embodiment, the MCP configuration specific to the sensor chip of the present invention is employed to integrate a small power generator that uses a MEMS variable capacitor, sensors, a microprocessor, a memory, a high frequency circuit, a power supply control circuit, etc. in a sensor chip to realize a compact and light-weight health care instrument. On the other hand, there is also a power generator or battery that can supply an electric power of 0.1 mW or so in a size roughly equal to that described above.

Figure 24A:
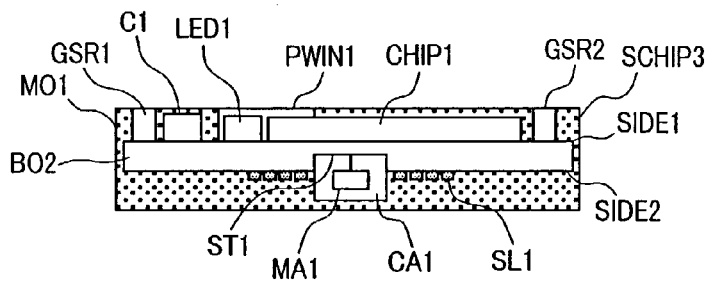
FIGS. 24A and 24B are sectional views of a power generator included in the sensor chip of the present invention, according to a third embodiment.
Figure 24B:
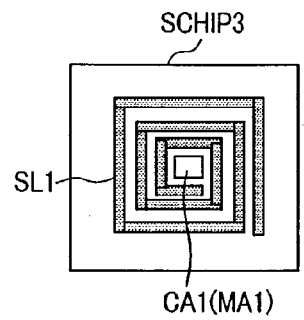

For example, FIGS. 24A and 24B show an example of a sensor chip that uses a power generator that makes good use of electromagnetic induction. FIG. 24A shows a side cross-sectional view of the chip and FIG. 24B shows a planar cross-sectional view of the chip. This power generator has the same configuration as that disclosed in the above-referenced document 11. A cavity CA1 is formed on the SIDE2 of the substrate BO2. A permanent magnet MA1 and a supporting member, such as a spring, for suspending the MA1 to the substrate BO2 are provided in the cavity CA1. In addition, a spiral type inductor SL1 is formed with a wiring pattern on the SIDE2 of the substrate BO2. The permanent magnet MA1, which is retained by the supporting member ST1, undergoes an inertial movement due to external vibration, and the inductor SL1 converts changes of the magnetic flux caused by this inertial movement to electrical energy on the basis of the principle of electromagnetic induction. And, if the ultra-low power consumption controlling method of the present invention as described in the first embodiment is employed here, it is possible to realize a compact sensor chip just like that in the first embodiment.

Figure 24C:
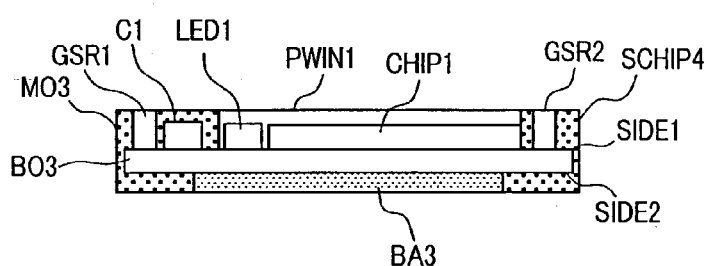
FIGS. 24C and 24D are sectional views of a power generator included in the sensor chip of the present invention, according to the third embodiment.
Figure 24D:
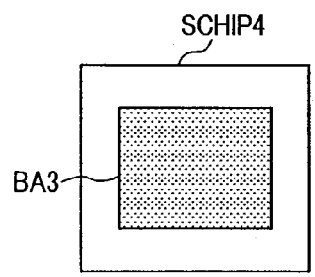

FIGS. 24C and 24D show an example of a sensor chip that uses a solar battery BA3. FIG. 24C shows a side cross-sectional view of the chip, while FIG. 24D shows a rear view of the chip. The solar battery is mounted on the SIDE2 of the substrate BO3. As shown in FIGS. 24C and 24D, the solar battery BA3 must be exposed in the mold MO3. Otherwise, an optical window must be formed on the battery BA3 using elements similar to those of the optical window PWIN1 that is formed in the upper portion of the CHIP1. The solar battery has a power generation capacity of 0.05 to 1 mW/cm2, although it depends on the irradiated light intensity. The solar battery is required to be irradiated with a light of a certain level during operation. As shown in FIG. 24C, the solar battery BA3 should preferably be disposed on the SIDE2, which is the back side of the SIDE1 that comes in contact with the target human body.

Figure 24E:
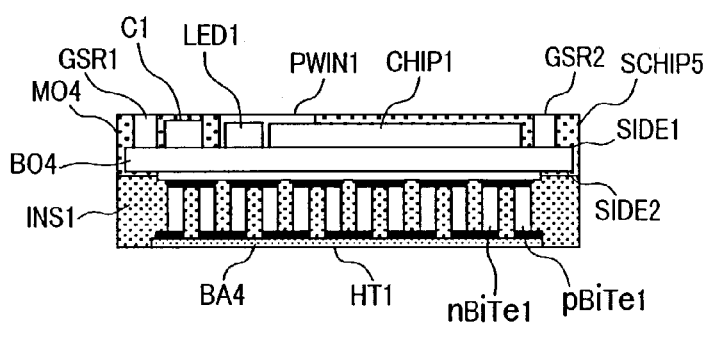
FIGS. 24E and 24F are sectional views of a power generator included in the sensor chip of the present invention, according to the third embodiment.
Figure 24F:
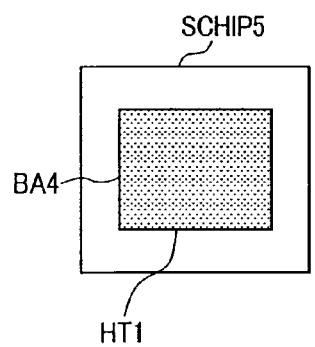

FIGS. 24E and 24F show an example of a sensor chip that uses a Seebeck element that can generate electric power from a temperature difference. FIG. 24E shows a side cross-sectional view of the chip, while FIG. 24F shows a rear view of the chip. The Seebeck element is configured by a PN junction consisting of an N-type Bite and a P-type Bite that are kinds of semiconductors. If a temperature difference is applied to the PN junction, an electromotive force (up to 20 mV) is generated there. This physical phenomenon is used to convert heat energy to electrical energy. As shown in FIG. 24E, in the sensor chip SCHIP5 of the present invention, the power generator BA4 that uses a Seebeck element is disposed on the SIDE2 of the substrate BO4. Both sides of this Seebeck element are connected to the substrate BO4 or to the outside air thermally through heat spreaders HT1, HT2 having favorable thermal conductivity characteristics, and a power is generated according to the temperature difference between them. As shown in FIG. 24E, therefore, the portion between the heat spreaders HT1 and HT2 must be insulated thermally with the use of an insulating material INS1. During actual operation, the heat spreader HT1 denotes the temperature of a human body and the heat spreader HT2 denotes the outside air temperature, as shown in FIG. 3. An electric power is thus generated by the difference between the user's body temperature and the outside air temperature.

Figure 24G:
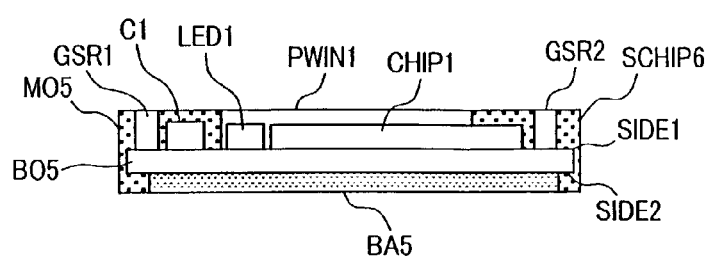
FIGS. 24G and 24H are sectional views of a power generator included in the sensor chip of the present invention, according to the third embodiment.
Figure 24H:
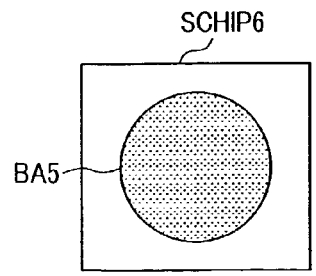

FIGS. 24G and 24H show an example of a sensor chip that uses a small button battery BA5. FIG. 24G shows a side cross-sectional view of the chip, while FIG. 24H shows a rear view of the chip. Unlike the examples shown in FIGS. 24A to 24F, the sensor chip in this example has no power generation mechanism, so that it cannot be used permanently. However, as is well known, even a button battery used for a wrist watch has a capacity (LR41) of 20 mAH or so. If such a button battery is used together with the ultra-low power consumption controlling method of the present invention, the sensor chip can be used for a few years without battery replacement.

According to this third embodiment, the sensor chip of the present invention can use various types of power generators or batteries. In addition, those different types of power generators or batteries may be combined in the sensor chip.

For example, the sensor chip of the present invention may be configured as a hybrid one, in which the MEMS variable capacitor type power generator shown in FIG. 1 is combined with a button battery shown in FIGS. 24G and 24H, whereby the power from the MEMS variable capacitor type power generator can be used for data detection, while the button battery can be used as an auxiliary power source for transmitting detected data to the outside wirelessly. And, when such a sensor chip configured as a hybrid one is used, the communication distance, as well as the transmission time, are extended easily.

Fourth Embodiment

In the above example, a description has been made for a case in which sensor data is transmitted to an external device (ex., the health care instrument shown in FIG. 3) directly through a low power RF transmission circuit that is built in the sensor chip. However, as described in connection with the first embodiment, the RF power for transmission is limited. Consequently, the wireless connection distance to the external device is usually set at 1 to 2 m. Even when a hybrid configuration is employed for the sensor chip that also uses a button battery, an attempt should be made to avoid an increase in the transmission power thoughtlessly, in consideration of the battery life. The small wireless relay chip of this embodiment is used to solve this problem.

Figure 25:
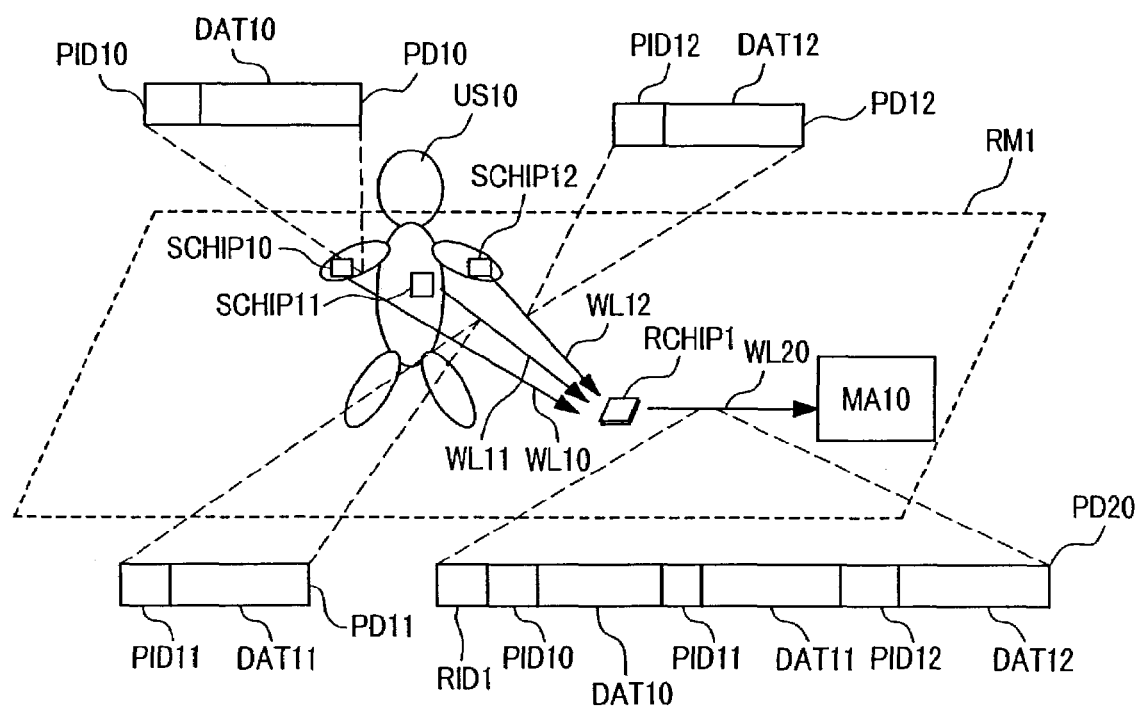
FIG. 25 is a diagram illustrating the concept of detected data relay by a wireless relay chip, according to a fourth embodiment.

FIG. 25 shows an example of such a small wireless relay chip. The small wireless relay chip RCHIP1 is attached to a floor or wall of a room RM1, and it receives packet data (PD10–PD13) from any of the sensor chips (SCHIP1–3) as described in the first to third embodiments and groups them into one data to be transferred (=relayed) to the external device MA10. A plurality of this type of wireless relay chip are usable to relay data sequentially, thereby extending the data transfer distance.

Figure 26:
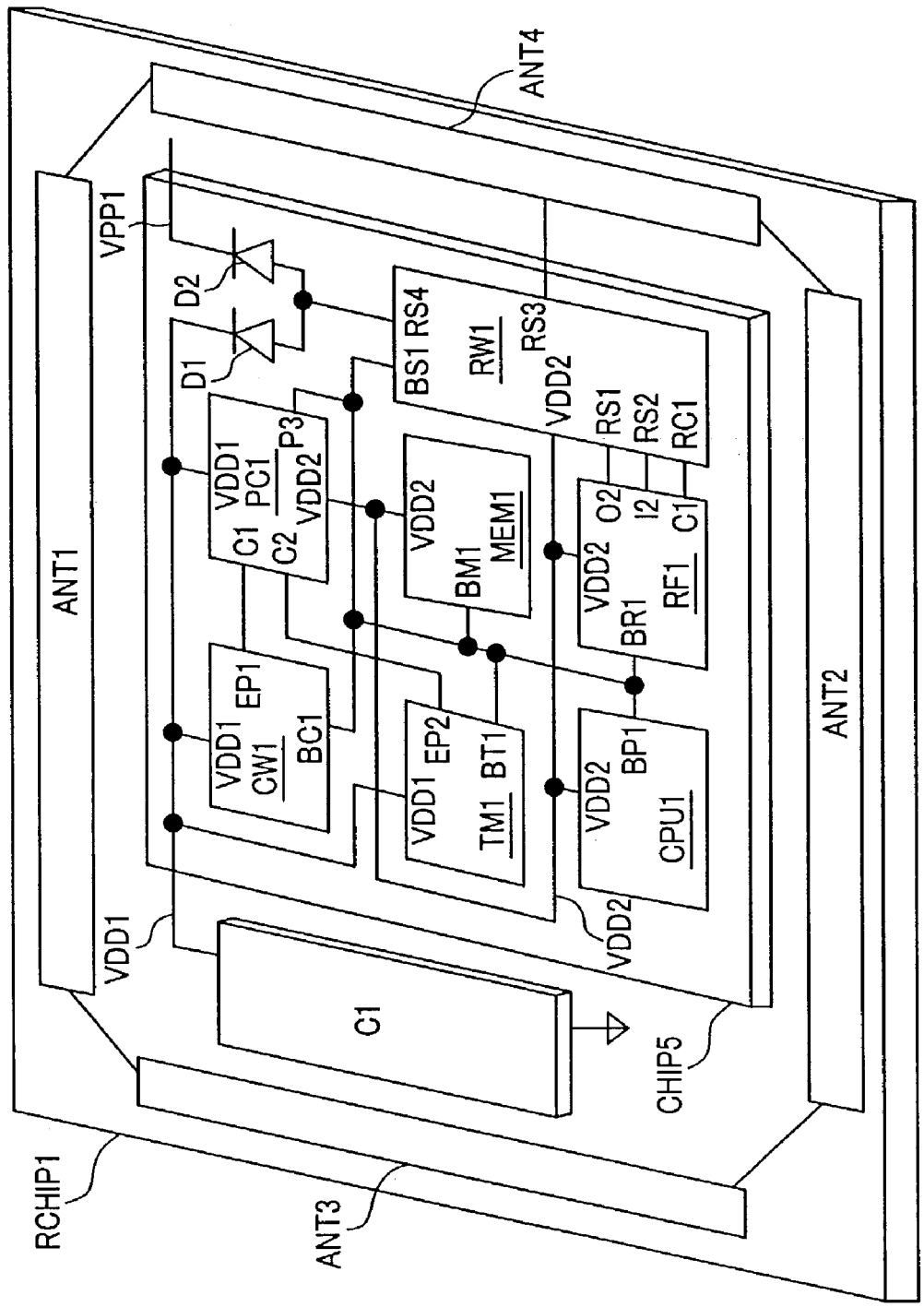
FIG. 26 is a diagrammatic perspective view of a wireless relay chip according to the fourth embodiment.

FIG. 26 shows a block diagram of a small wireless relay main chip that is disposed on a surface (SIDE1) of the chip. Although not shown in FIG. 26, the MEMS variable capacitor power generation chip shown in FIG. 1B, the power generator, or the battery shown in FIGS. 24A through 24D is usually integrated on the SIDE2, which is the back side in the MCP configuration. An antenna, a capacitor, and other circuits may also be integrated together. This chip may also be operated as a single unit without using any special power source.

As shown in FIG. 26, the CHIP5 that is characteristic of the present invention is configured by a microprocessor CPU1, a memory MEM1, a high frequency transmission/reception circuit RF1, an electrical charge monitoring circuit CW1, a timer TM1, and a power supply control circuit PC1. The circuits are configured similarly to those of the main chip CHIP1 described in connection with the first embodiment.

Figure 27:
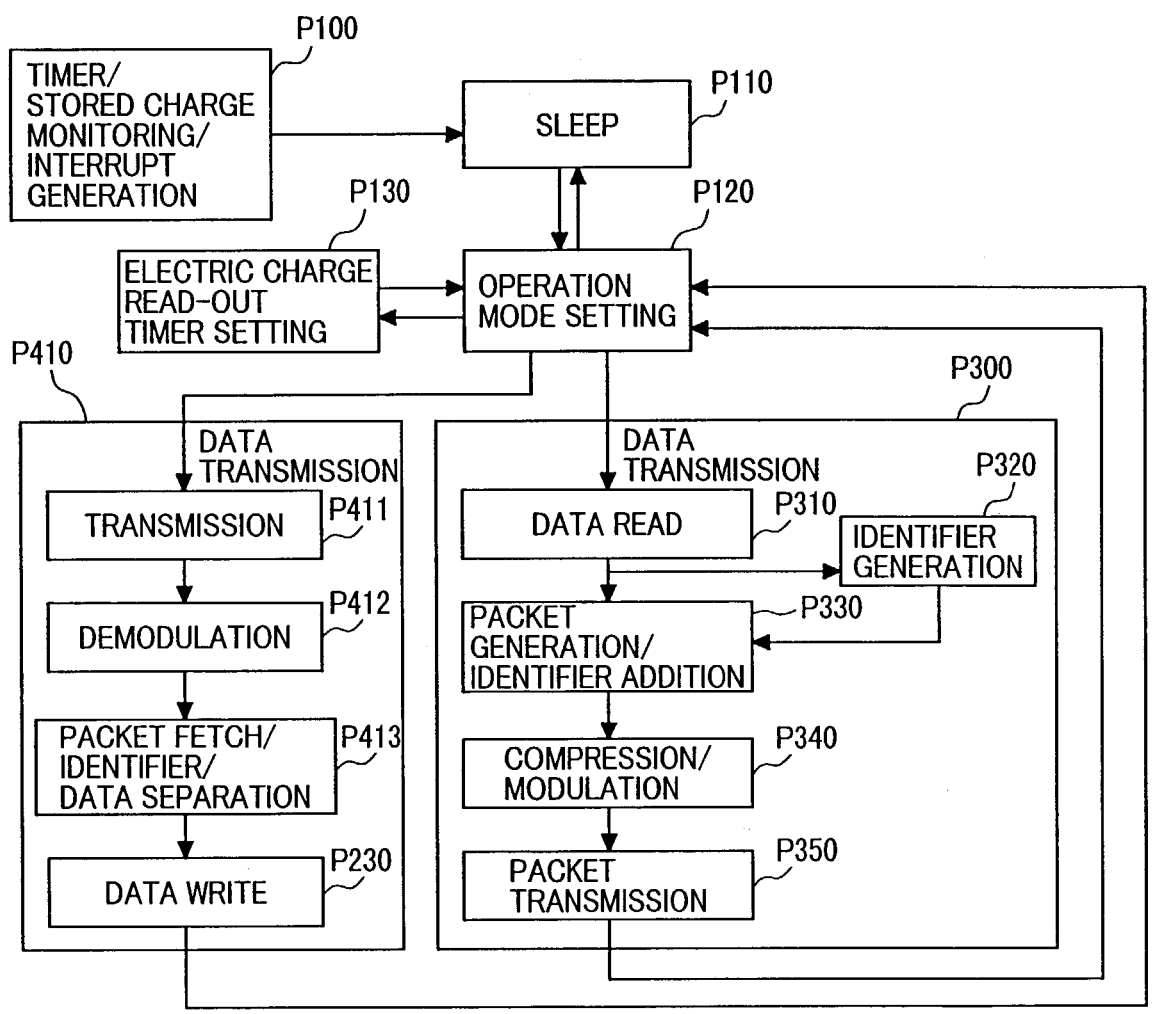
FIG. 27 is a flowchart of the operation of the wireless relay chip shown in FIG. 26.

FIG. 27 shows a flowchart of the operation of the small wireless relay chip. The relay chip usually is in a sleep state (P110) due to use of the low power consumption operation method, similar to that of the sensor chip described in connection with the first embodiment. The relay chip is activated intermittently by an interrupt signal from any of the timer TM1 and/or the electric charge monitoring circuit CW1, so that data is received (P410) and transmitted (P120). In the flowchart shown in FIG. 25, data reception (P410) must be started up more frequently than data transmission (P120). This is to avoid a failure of data reception from any of the sensor chips CHIP1 to CHIP3. Even when the activating frequency of the data reception (P410) is set to be higher, no problem will arise, since the power consumption of the data reception is low.

In the P320 routine shown in FIG. 27, it is also possible to add an ID (RID20) specific to this wireless relay chip to the sensor data from the sensor chip. As will be described in connection with a fifth embodiment, if this relay chip ID is taken out at the data receiving side, it is possible to identify the route used to receive the data.

Fifth Embodiment

Next, an example of the sensor chip or wireless relay chip of the present invention will be described with reference to FIGS. 28 to 28C.

Figure 28A:
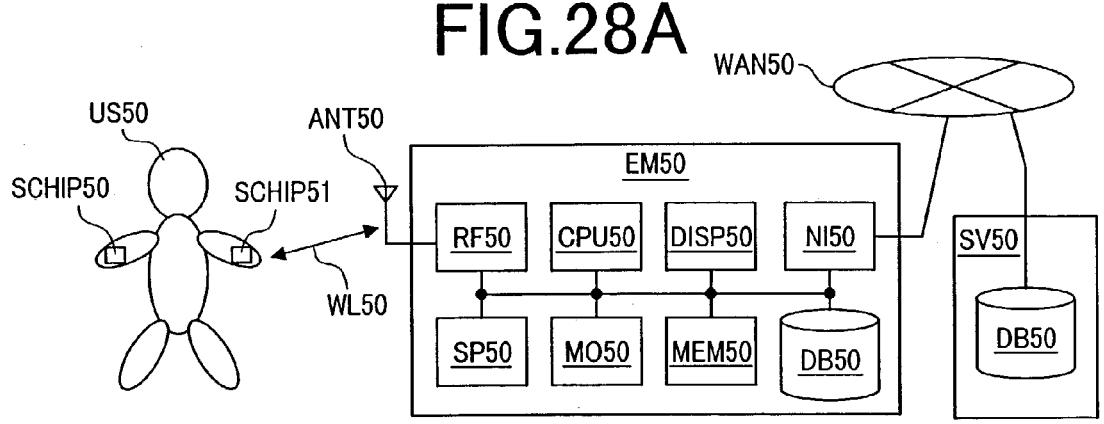
FIG. 28A is a diagram showing an example of the sensor chip of the present invention and the wireless relay chip according to a fifth embodiment.

FIG. 28A shows an example of the use of the sensor chip of the present invention for controlling a device (EM50), such as a home electrical appliance, a game device, a toy robot, etc. As shown in FIG. 28A, when a user US50 uses the device EM50, the user US50 first sticks the sensor chips CHIP50 and CHIP51 on his/her body, for example, as shown in FIG. 3. The device EM50 is configured by an RF50 for receiving control signals from the sensor chips SCHIP50 and SCHIP51 through a wireless connection device WL50; a microprocessor CPU50 for setting the operations of the EM50 and/or operation parameters according to received control signals; a memory MEM50; a display unit DISP50; a data base DB50; a network interface NI50 for connecting the EM50 to a portable telephone network or a wide ranged network, such as the Internet; and a motor MO50 for moving the device EM50. As an example, the device EM50 is assumed to be a toy electronic robot. In this regard, the device EM50 changes its motions according to the user information detected by the sensor chips SCHIP50 and SCHIP51 of the present invention, as if each of the motions is made in response to a user's request, thereby making a highly intelligent motion.

Specifically, the CPU50 estimates the user's feelings or mental state according to the blood pulse information and GSR information obtained from the blood pulse sensor or impedance sensor disposed in the sensor chip of the present invention. When it is determined that the user is sad, for example, the motor 50 is started to perform an action to comfort the user. When it is determined that the user is nervous, the device outputs, for example, chirping of birds from its built-in speaker SP50 to make the user relax. In addition, it is also possible to make the device turn in the user's requested direction according to a user's motion, such as hand waving, as detected by the acceleration sensor disposed in the sensor chip. In addition, information such as hand waving can also be used instead of a button input to a home electric appliance. The range of application of the sensor chip of the present invention is very wide.

The examples described above are just typical ones. The user's living body information may also be used for controlling various home electric appliances. For example, an air conditioner's setting can be changed according to the user's body temperature with the use of the sensor chip of the present invention.

Figure 28B:
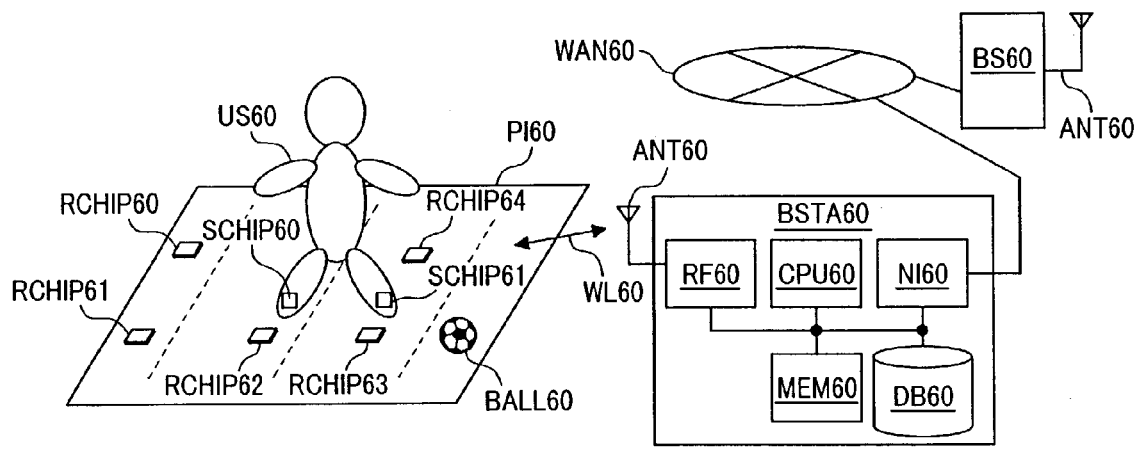
FIG. 28B is a diagram showing an example of the sensor chip of the present invention and the wireless relay chip according to the fifth embodiment.

FIG. 28B shows an example of the use of the sensor chip and the wireless relay chip of the present invention for recording the results of sports games, such as soccer, etc. In this example, a soccer player US60 attaches the sensor chips (SCHP60 and SCHIP61) to his/her legs. Information detected by the SCHIPs 60 and 61 is received by the wireless relay chips RCHIPs 60 to 64 of the present invention, that are disposed at fixed intervals in a soccer field P160, while a wireless relay chip ID is added to the information concerning the player as described in connection with the fourth embodiment. Finally, the information is received by a base station BSTA60. The base station BSTA60 is configured by an RF60 for receiving sense data from each of the wireless relay chips RCHIP60–64 through a wireless connection device WL60; a microprocessor CPU60 for analyzing sense data to analyze the motion of the player or such health conditions as the user's blood pulse, etc.; a memory MEM60; a data base DB60; and a network interface N160 for connecting the base station BSTA60 to a portable telephone network, the Internet, or a wide range network WAN60, such as a dedicated network. The base station BSTA60 analyzes packet data and identifies the location of the information originating sensor chip from the relay chip ID added to the wireless relay chip, thereby identifying a point of the field at which the player exists in real time. At the same time, the fatigued condition of the player can be estimated from the living body information, such as detected blood pulses, etc. For example, such information is usable for the timing of player substitutions. In addition, if analyzed information is transferred through a wide range network WAN60, the information is usable effectively for TV broadcasting at a TV station, such as the BS60 connected to the WAN.

While the description here is directed to a soccer game, the sensor chip can also be used for other games and matches of sports events, of course. The sensor chip and the wireless relay chip of the present invention can thus be used effectively for various games and matches of sports events, so as to monitor the position of each player in real time. Conventionally, devices for detecting the motions of animals, such as mice for experiments, with the use of an RFID chip have also been proposed. When the sensor chip is used in a wide area, such as a soccer field, however, a great number of expensive RFID readers are needed. This has been a problem. There is also another problem in that the power consumption becomes significant in such a case. On the other hand, the sensor chip and the wireless relay chip of the present invention individually require only very low power consumption. The use of the sensor chip/wireless relay chip of the present invention in such a way thus makes it possible to provide a sports game recording apparatus that is capable of practical use.

Figure 28C:
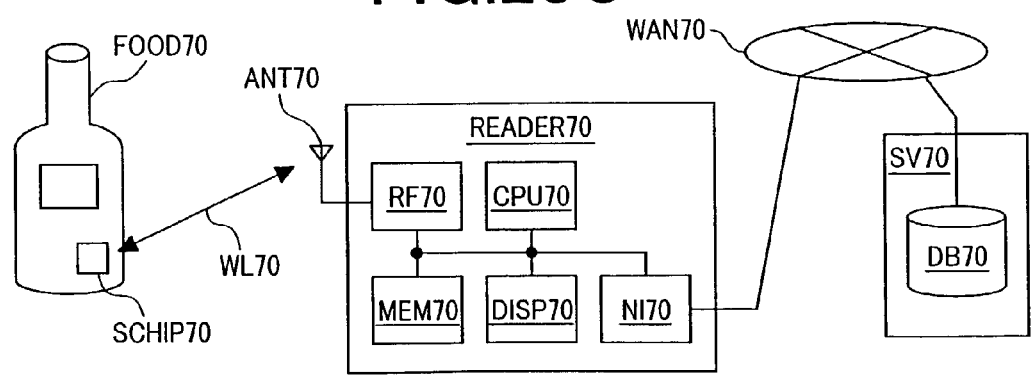
FIG. 28C is a diagram showing an example of the sensor chip of the present invention and the wireless relay chip according to the fifth embodiment.

FIG. 28C shows an example of the use of sensor chip of the present invention for food distribution management. As shown in FIG. 28C, the sensor chip of the present invention is stuck onto a food container FOOD70. The food container FOOD70 may be a container for wine or beer, for example. As shown in FIG. 28C, the sensor chip of the present invention is stuck on the wine or beer bottle. And, as described in connection with the first embodiment, the sensor is driven for a certain time so that the temperature of the bottle is measured by the built-in sensor continuously and the result is stored in the memory MEM70. Finally, when the bottle is delivered to a consumer, the information stored in the memory is read with the use of a reader READER70. The READER70 is configured by an RF70 for reading detected data from the sensor chip through a wireless connection device WL70, a microprocessor CPU70 for analyzing the read data and displaying the result, a memory MEM70, and a display unit DISP70. This READER70 may have a built-in network device N170, which is used to access the data base DV70 located in the data management server SV70 through the N170 or a wide range network WAN70, such as a portable telephone network, the Internet, etc. In other words, the received sensor chip ID is referred to in the data base DB70 which is located in the server SV70, so that the user obtains the information of the FOOD70 producer.

There is also a conventional device provided with an RFID and a battery, which realizes management of distribution of beer barrels. Unlike the sensor chip of the present invention, however, it has been difficult to reduce the size of the device enough to allow it to be stuck on wine or beer bottles. In addition, because the conventional device is driven by a battery, data reception is disabled when the battery is used up. The device thus is characterized by a limited data collection period. This is why the conventional device has been used only for beer barrels of the type delivered to restaurants and the like, which are collected comparatively quickly. On the contrary, the sensor chip of the present invention can be stuck on small objects, such as wine bottles, etc. In addition, the sensor chip will keep working to collect information for a long time. Thus, the sensor chip can also be used with various objects other than beer barrels to be delivered to restaurants and the like.

While the present invention has been described with reference to the first to fifth embodiments, the present invention is not limited only to those embodiments. It is to be understood that modifications will be apparent to those skilled in the art without departing from the spirit of the invention.

For example, while a sensor chip provided with a wireless transmission/reception circuit has been described with reference to the above embodiments, the sensor chip is not required to receive data wirelessly. In such a case, the sensor chip is provided only with a transmission circuit. Consequently, the receiving circuit may be omitted from such a sensor chip.

Furthermore, in the above embodiments, a description has been made of a sensor chip provided with a temperature sensor TD1, an acceleration sensor AS1, a red/infrared light sensor PD1, and an impedance sensor GS1. However, the sensor chip need not necessarily be provided with all of those sensors. The sensor chip may be provided only with some of them to meet the design use and purpose, or it may be provided with sensors other than those described above.

Furthermore, in the above embodiments, the sensor chip is directed for use mainly for human beings. However, the sensor chip may be used for dogs, cats, and other animals, as well.

Because the sensor chip of the present invention is provided with various sensors, as well as a microprocessor, a memory, a transmission circuit, and a power generator, the employment of the sensor chip makes it possible to provide a semiconductor device that is employable for a compact and light-weight sensor system that can operate continuously for a long time.

Furthermore, the semiconductor device for a sensor system is compact, light-weight, and free of the need for battery replacement. The semiconductor is thus favorable for use in such devices as a health care instrument, etc. that must be operated for a long time. Furthermore, the semiconductor may also apply to any of such devices as toy electronic robots with which the users can communicate, remote-control devices by which the users can report their requests to target home electric appliances, etc., as well as recording devices for recording information related to games/matches of sports events, and recording devices for monitoring and recording temperatures of foods on their distribution routes.

What is claimed is:

1. A semiconductor device, comprising:
   a sensor for detecting a physical quantity of an object to be measured;
   an A/D conversion circuit for amplifying a signal detected by said sensor and for converting the amplified signal to a digital signal;
   a microprocessor for processing said digital signal;
   a memory for storing information based on said digital signal;
   a transmission circuit for transmitting said digital signal processed by said microprocessor to the outside; and
   a power generator for generating electric power to be supplied to said sensor, said A/D conversion circuit, said microprocessor, said memory, and said transmission circuit, respectively,
   wherein said semiconductor device further includes a power supply control circuit and a capacitor;
   wherein said power supply control circuit is configured so as to control whether to supply electric power generated by said power generator to said sensor, said A/D converter, said microprocessor, said memory, and said transmission circuit; and
   wherein said capacitor is configured so as to accumulate said electric power generated by said power generation unit.

2. The semiconductor device according to claim 1,
   wherein said sensor, said A/D conversion circuit, said microprocessor, said memory, and said transmission circuit are formed on one side of a semiconductor substrate.

3. The semiconductor device according to claim 2,
   wherein said transmission circuit is configured so as to transmit signals as pulse strings through a UWB (Ultra Wide Band), which employs an ultra wide band radio communication method.

4. The semiconductor device according to claim 2,
   wherein said power generator is formed on the other side of said semiconductor substrate, which is the side opposite said side on which said sensor unit, said A/D conversion circuit, said microprocessor, said memory, said transmission/receiving circuit, and said power supply control circuit are formed.

5. The semiconductor device according to claim 2, comprising a mounting substrate,
   wherein said semiconductor substrate is disposed on a first main surface of said mounting substrate; and
   wherein said power generator is disposed on a second main surface of said mounting substrate, which is the side opposite said first main surface.

6. The semiconductor device according to claim 2,
   wherein said power generator is a variable capacitor formed in an MEMS (Micro Electro Mechanical System) process.

7. The semiconductor device according to claim 2,
   wherein said power generator generates electric power from vibration.

8. The semiconductor device according to claim 2,
   wherein said power generator generates electric power from light energy.

9. The semiconductor device according to claim 2,
   wherein said power generator generates electric power from a temperature difference.

10. The semiconductor device according to claim 2,
    wherein said power generator is a button battery.

11. The semiconductor device according to claim 2,
    wherein said power generator comprises an electric generator and a battery.

12. The semiconductor device according to claim 2,
    wherein said sensor is a temperature sensor; and
    wherein said semiconductor device has a diode used as said temperature sensor.

13. The semiconductor device according to claim 2,
    wherein said sensor is an acceleration sensor; and
    wherein said acceleration sensor is formed in said MEMS process.

14. The semiconductor device according to claim 2,
    wherein said sensor is an optical sensor; and
    wherein said optical sensor is covered by a material that transmits red or infrared rays.

15. The semiconductor device according to claim 2,
    wherein said memory stores a specific ID number.

16. The semiconductor device according to claim 2,
    wherein said semiconductor device has a seal; and
    wherein said seal is configured so as to be stuck on an object to be detected.

17. A semiconductor device, comprising:
    a sensor chip that includes a temperature sensor, an acceleration sensor, and a red/infrared ray sensor;
    an A/D conversion circuit for amplifying a signal received from said sensor chip and for converting said signal to a digital value;
    a microprocessor for taking out information from said sensor chip to process said information;
    a memory for storing a program code of said microprocessor and said information received from said sensor chip;
    a transmission circuit controlled by said microprocessor and used to transmit data to the outside;
    a power supply control circuit for controlling whether to supply electric power to said sensor unit, said A/D conversion circuit, said microprocessor, said memory, and said transmission circuit, respectively; and
    a power collection circuit for collecting an increase of electrostatic energy of a variable capacitor generated by mechanical vibration to convert said increase to electrical energy,
    wherein said sensor chip, said A/D conversion circuit, said microprocessor, said memory, said transmission/receiving circuit, and said power supply control circuit are formed on one side of a semiconductor substrate.

* * * * *